US009938570B2

(12) United States Patent
Spier

(10) Patent No.: US 9,938,570 B2
(45) Date of Patent: Apr. 10, 2018

(54) METHODS AND COMPOSITIONS FOR UNIVERSAL DETECTION OF NUCLEIC ACIDS

(71) Applicant: UniTaq Bio, Los Altos, CA (US)

(72) Inventor: Eugene Spier, Los Altos, CA (US)

(73) Assignee: UNITAQ BIO, Los Altos, CA (US)

( * ) Notice: Subject to any disclaimer, the term of this patent is extended or adjusted under 35 U.S.C. 154(b) by 0 days.

(21) Appl. No.: 14/566,596

(22) Filed: Dec. 10, 2014

(65) Prior Publication Data
US 2015/0167067 A1 Jun. 18, 2015

Related U.S. Application Data

(62) Division of application No. 12/931,803, filed on Feb. 9, 2011, now Pat. No. 8,940,487.

(60) Provisional application No. 61/302,876, filed on Feb. 9, 2010, provisional application No. 61/308,982, filed on Feb. 28, 2010.

(51) Int. Cl.
*C12Q 1/68* (2018.01)

(52) U.S. Cl.
CPC ........... *C12Q 1/6853* (2013.01); *C12Q 1/686* (2013.01); *C12N 2310/141* (2013.01)

(58) Field of Classification Search
None
See application file for complete search history.

(56) References Cited

U.S. PATENT DOCUMENTS

| 5,487,972 A | 1/1996 | Gelfand et al. |
| 5,494,810 A | 2/1996 | Barany et al. |
| 5,723,591 A | 3/1998 | Livak et al. |
| 5,866,336 A | 2/1999 | Nazarenko et al. |
| 5,994,056 A | 11/1999 | Higuchi |
| 6,270,967 B1 | 8/2001 | Whitcombe et al. |
| 6,277,607 B1 | 9/2001 | Tyagi et al. |
| 6,670,461 B1 | 12/2003 | Nielsen |
| 2010/0143898 A1 | 6/2010 | Kutyavin |

OTHER PUBLICATIONS

Thelwell et al. (2000) "Mode of action and application of Scorpion primers to mutation detection." *Nucleic Acids Research*, 28(19): 3752-3761.
Whitcombe et al. (1999) "Detection of PCR products using selfprobing amplicons and fluorescence." *Nature Biotechnology*, 17: 804-807.
European Search Report, dated Jul. 12, 2013 for application No. 11742575.1.
Theiwell et al. (2000) Mode of action and application of scorpion primers to mutation detection. *Nucleic Acids Research*, 28(19): 3752-3761.

*Primary Examiner* — Nancy A Treptow
(74) *Attorney, Agent, or Firm* — Quine IP Law; Gary Baker

(57) ABSTRACT

Provided are methods and compositions for detecting the presence or amount of one or more target nucleic acids in a sample. Methods of the present invention include linking universal nucleic acid segments into a single molecule in a linking reaction dependent on a target nucleic acid of interest. A variety of universal segment linking strategies are provided, including preamplification by polymerase chain reaction, ligation-based strategies, reverse transcription and linear polymerase extension. Linking the universal segments into a single molecule generates a tagged target nucleic acid which is detected in a manner dependent on an intramolecular interaction between one universal segment and a second portion of the tagged target nucleic acid. In certain embodiments, the intramolecular interaction includes the formation of a hairpin having a stem between a universal segment at one end of the tagged target nucleic acid and a second universal segment at the opposite end of the tagged target nucleic acid. A variety of detection formats are provided, including solution-phase and surface-based formats. The methods and compositions are well-suited for highly multiplexed nucleic acid detection, and are applicable for the detection of any target nucleic acid of interest in both research and clinical settings.

29 Claims, 26 Drawing Sheets

METHODS AND COMPOSITIONS FOR UNIVERSAL DETECTION OF NUCLEIC ACIDS

CROSS-REFERENCE TO RELATED APPLICATIONS

This application is a divisional of U.S. Ser. No. 12/931,803 filed Feb. 9, 2011 (now allowed), which is a non-provisional utility patent application claiming priority to and benefit of the following prior provisional patent applications: U.S. Ser. No. 61/302,876, filed Feb. 9, 2010, entitled "Methods for nucleic acids detection using universal hairpin forming primers and its applications" by Eugene Spier; and U.S. Ser. No. 61/308,982, filed Feb. 28, 2010, entitled "Methods for nucleic acids detection using universal hairpin forming primers" by Eugene Spier. Each of these provisional applications is incorporated herein by reference in its entirety for all purposes.

BACKGROUND OF THE INVENTION

Traditional methods to detect DNA in a sample using polymerase chain reaction (PCR) detect double-stranded DNA, e.g., SYBR (Higuchi, U.S. Pat. No. 5,994,056) or use probe based detection. Examples of the latter method include TAQMAN™ (Gelfand et al., U.S. Pat. Nos. 5,210,015 and 5,487,972 and Livak et al., U.S. Pat. No. 5,723,591) and molecular beacons (Tyagi et al., International Publication No. WO 1995/013399). In TAQMAN™, a probe molecule that includes a fluorescent label and a quencher hybridizes to a PCR amplification product and is digested by the 5' exonuclease activity of a polymerase. The 5' exonuclease activity releases the fluorescent label from the probe, thereby separating the fluorescent label from the quencher and permitting detection of the fluorescent signal. One application of TAQMAN™ detection that finds use in SNP genotyping is described by Livak et. al (U.S. Pat. No. 5,538,848). The molecular beacons method utilizes a probe molecule having a stem-loop structure that keeps a fluorescent label and a quencher in close proximity. The probe molecule opens up upon binding to its complementary target, decreasing the quenching so that the fluorophore emits more light proportional to the number of target molecules amplified at a given cycle.

Whitcombe et al. describe the "Scorpion" method for DNA detection (U.S. Pat. No. 6,326,145 and 2005/0164219). This method employs a PCR primer with a 5' tail that has a dye and a quencher. The 3' end of the primer matches the target DNA in the sample, but the 5' tail is complementary to the target amplicon this primer generates upon extension. Thus, the primer extension product forms a hairpin during PCR resembling a scorpion, and a fluorescent signal can be detected using the 5' nuclease (e.g., TAQMAN™), molecular beacon or other method. Whitcombe et al. (Nature Biotechnology (1999) 17:804-807) describe unimolecular scorpion detection using "sunrise" primers that form a hairpin that brings a dye and a quencher close to each other; after primer extension, another hairpin forms with the dsDNA stem that increases the distance between the dye and the quencher. Thelwell et al. (Nucleic Acid Research (2000) 28: 3752-61) compared scorpion "molecular beacon" and 5' nuclease detection with TAQMAN™ and showed that unimolecular scorpions give stronger signal than bimolecular TAQMAN™. Solinas et al. (Nucleic Acids Research (2001) 29(2):e96) compared molecular beacon and duplex scorpion with the quencher on a separate oligo and found that the latter provided larger signal difference between the quenched and unquenched states. The advantage of the scorpion method is that there is no separate probe molecule required to anneal to the amplicon (bimolecular interaction) and intramolecular hairpin formation has kinetic and thermodynamic (using the same probe versus hairpin stem sequence) advantages over intermolecular interactions. Using the scorpion method, hairpin formation will nearly always precede PCR primer annealing, whereas primer annealing often precedes probe to template annealing, leading to a decrease in detectable signal. For a review of various approaches for generating a detectable signal during quantitative PCR, as well as Cycling Probe Technologies (CPT)-based FEN, invader-type signal generation, and 5' nuclease FRET signal, see Kutyavin, International Publication No. WO 2007/127999.

Methods that utilize universal primers and separate probes for nucleic acid detection have been described. For example, see Whitcombe et al. (U.S. Pat. No. 6,270,967) and Anderson et al. (U.S. Pat. No. 7,601,821). A drawback of these methods is that they are prone to generate non-specific signal. In these methods, a fluorescent signal is generated even if a single primer is involved in amplification. These methods generally use a multiplex pre-amplification (encoding), so inevitably primer dimers and non-specific amplifications occur. Even after the dilution that usually follows the pre-amplification step, these non-target amplicons and unused pre-amplification primers are still present in the mixture. Single primer specificity makes it more difficult to develop applications with "clean NTC" ("non template control") signal.

The drawbacks of previously described detection methods that utilize target-specific primers and probes are cost and logistics. Scorpion approaches require a specific dual-labeled primer for each target nucleic acid (e.g., see U.S. Pat. No. 6,326,145), making these approaches quite expensive, especially when detection of multiple targets is required. For example, there are approximately 25,000 human genes and more than 10 million human single nucleotide polymorphisms (SNPs), and researchers often need to measure expression levels or determine the genotypes for tens, hundreds, or sometimes even thousands of targets. Furthermore, each user or research team/project generally requires a different set of genes/SNPs.

Several dyes are currently available as amidites, e.g., VIC and FAM. It is relatively inexpensive to manufacture oligonucleotides ("oligos") with these dyes, as all of the oligo synthesis steps are performed on a column. There is a broad choice of fluorescent dyes that can be incorporated into oligos, but they require off-column dye attachment, e.g., CY3™, CY5™, and TEXASRED™. This makes oligo manufacturing more expensive, and often impractical, when each target requires a custom synthesis. Universal detection assays described hereinbelow amortize the oligo synthesis cost over multiple customers and experiments making it cost-effective to use the "off-column" dyes. Several commercial vendors preload assays in wells to simplify lab work for customers, e.g., TAQMAN™ low-density arrays and BIOTROVE™ from Life Technologies and SUPERARRAYS™ from Qiagen. Most customers require a custom set of assays, making manufacturing logistics for target-specific assays complicated. As described in detail herein, the present invention permits universal sets of assays for detecting any set of nucleic acid targets, making it much easier to offer preloaded assays: the same preloaded assays can be used to detect any set of targets. In addition, the present invention separates the encoding and detection steps, providing flexibility to detect multiple targets in the same color (in the same or different reaction volume), see, e.g., the examples for detecting trisomy 21 and HIV drug resistance mutations hereinbelow. Finally, unlike other universal detection methods, the present invention has two primer plus virtual probe specificity, rather than only two primer specificity for previously described universal detection formats.

Exiqon and Roche have developed the UNIVERSAL PROBELIBRARY™ (UPL) for gene expression that uses a set of 165 short 8-9 base universal probes (see Roche Applied Science website). These short probes have several locked nucleic acids (LNA, U.S. Pat. No. 6,670,461) that exhibit a high melting temperature when hybridized to DNA, in spite of being short. The universal probes also have normal DNA bases at the 5' end so that they can be cleaved by the 5'-nuclease activity of a polymerase during PCR. The universal probes limit possible PCR primer locations in genes. However, the 165 universal probe set has sufficient occurrences in most mRNA sequences to enable choosing PCR primers such that at least one of the 165 universal sequences can be located between the two primers. The detection assays, however, are not universal, as each gene expression assay requires two target-specific primers.

Due to the above-noted drawbacks of current detection strategies (e.g., specificity, cost, manufacturing logistics, and the like), there is a need for more specific, flexible, and cost-effective methods of nucleic acid detection. The present invention meets these and a variety of other needs.

SUMMARY OF THE INVENTION

The present invention generally provides methods and compositions for detecting the presence or amount of one or more target nucleic acids in a sample. Methods of the present invention include linking universal nucleic acids segments into a single molecule in a linking reaction dependent on a target nucleic acid of interest. A variety of universal segment linking strategies are provided, including preamplification by polymerase chain reaction, ligation-based strategies, reverse transcription and linear polymerase extension. Linking the universal segments into a single molecule generates a tagged target nucleic acid which is detected in a manner that uses an intramolecular interaction between a segment of a first universal primer and a segment of the tagged target nucleic acid. In certain embodiments, the intramolecular interaction includes the formation of a hairpin having a stem between a universal segment at one end of the tagged target nucleic acid and a second universal segment at the opposite end of the tagged target nucleic acid. A variety of detection formats are provided, including solution-phase and surface-based formats. The methods and compositions are well-suited for highly multiplexed nucleic acid detection, and are applicable for the detection of any target nucleic acid of interest in both research and clinical settings.

In a first aspect, the present invention provides a method of detecting the presence or amount of a first target nucleic acid in a sample, the method including linking first and second universal DNA segments into a first molecule in a linking reaction dependent on the first target nucleic acid, thereby providing a first tagged target nucleic acid. The first tagged target nucleic acid is PCR amplified using first and second universal primers, each universal primer having a 3' portion that anneals to one of the two universal DNA segments. The 3' portion of the first universal primer anneals to the first universal segment and a 5' portion of the first universal primer includes a nucleic acid sequence substantially identical to a portion of the first universal DNA segment, a portion of the second universal DNA segment, or a portion of the first target nucleic acid. An amplicon generated upon extension of the first universal primer forms an intramolecular hairpin stem between the 5' portion of the first universal primer and a portion of the amplicon complementary to the first universal DNA segment, the second universal DNA segment, or the first target nucleic acid. Alternatively, the first universal primer forms a circular structure upon annealing to the first tagged nucleic acid that brings the 3' and 5' ends of the first universal primer within close proximity to each other. Formation of the hairpin stem or circular structure results or causes a change in a first detectable signal, the first detectable signal indicating the presence or quantity of the first target nucleic acid in the sample.

The first target nucleic acid includes a nucleic acid or nucleic acid feature selected from: a DNA, an RNA, a mammalian nucleic acid, a primate nucleic acid, a rodent nucleic acid, a viral nucleic acid, a bacterial nucleic acid, an archaea nucleic acid, a cDNA, a cDNA corresponding to a short RNA, a bisulphite treated DNA, a genetic variant, a mutation or insertion that confers drug resistance, a somatic mutation, a polymorphism, a single nucleotide polymorphism, a rare allele, a portion of the KRAS gene, a nucleic acid that exhibits a variation in copy number, an intron, an exon, an intron-exon boundary, a splice junction, one or more dinucleotides corresponding to one or more methylated or unmethylated CpG dinucleotides, a nucleic acid comprising one or more restriction enzyme recognition sequences, a portion of human chromosome 21, a portion of the human X chromosome, and a portion of the human Y chromosome.

The present invention provides a number of approaches for linking the first and second universal DNA segments into a first molecule to generate the first tagged target nucleic acid. In a first embodiment, the linking reaction includes a PCR reaction that includes: a first primer having a 3' portion that anneals to a first portion of the first target nucleic acid and a 5' portion including the first universal DNA segment; and a second primer having a 3' portion that anneals to a second portion of the first target nucleic acid and a 5' portion including the second universal DNA segment. Amplification of the first target nucleic acid using the first and second primers links the first and second universal DNA segments into a single molecule.

The linking reaction can include a ligation reaction, where oligonucleotides complementary to the first target nucleic acid include 5' and 3' ends extending beyond the first target nucleic acid, and where the oligonucleotides serve as a template to ligate the first and second universal DNA segment to the first target nucleic acid. Other ligase-based strategies are provided. For example, the linking reaction can include a ligation reaction, where the first universal DNA segment is ligated to the second universal DNA segment on the first target nucleic acid, thereby linking the first and second universal DNA segments together into a single molecule.

Linking the first and second universal DNA segments into a first molecule can also be accomplished by reverse transcription. In this aspect, the reverse transcription reaction includes generating a first cDNA strand by extending a first primer having a 3' portion that anneals to a first portion of the first target nucleic acid and a 5' portion that includes the first universal DNA segment, where the target nucleic acid is an RNA. A second cDNA strand is generated by extending a second primer having a 3' portion that anneals to a portion of the first cDNA and a 5' portion that includes the second universal DNA segment. Synthesis of the first and second cDNA strands links the first and second universal DNA segments into a single molecule.

Linear polymerase extension can be employed in accordance with the present invention to link the first and second universal DNA segments into a first molecule. In this aspect, the first universal DNA segment is linked to the first target nucleic acid by a polymerase that extends on the template complementary to the first universal DNA segment. A primer with a 5' tail that includes the second universal DNA segment introduces the second universal DNA segment, thereby linking the first and second universal segments into a single molecule. Preferably, the 3' end of the first target nucleic acid is defined, e.g., after digestion by a restriction enzyme.

As will be appreciated, the methods and compositions of the present invention are well suited for the detection of multiple target nucleic acids simultaneously, either in the same reaction volume or separate reactions. In accordance with the present invention, the universal segment linking step can be multiplexed such that multiple target nucleic acids of different nucleic acid sequences are tagged with the same or different pairs of universal DNA segments. The different pairs of universal primers are optionally labeled with different dyes, the different dyes having different emission wavelengths, and during the detection step, the different dyes having different emission wavelengths are detected separately. Optionally, the target nucleic acids of different nucleic acid sequences are tagged with the same pair of universal DNA segments. When the universal primers are labeled with different dyes with different wavelengths and are detected separately, the first universal primer optionally includes a 5' portion that is substantially identical to a first strand of an internal portion of the tagged target nucleic acid, the second universal primer comprises a 5' portion that is substantially identical to the strand of the internal portion of the tagged target nucleic acid, and amplification of both strands of the tagged target nucleic acid is measured independently using two or more colors. According to this aspect, the target nucleic acid can include two closely spaced polymorphisms or methylation sites, where the two closely spaced polymorphisms or methylation sites are haplotyped using four colors.

The linking step can include linking n and n+1 universal DNA segments into one or more additional molecules in a linking reaction specific to one or more additional target nucleic acids, thereby providing one or more additional tagged target nucleic acids in a single reaction volume, where n is a third or higher number. For example, the linking step can further include linking third and fourth universal DNA segments into a second molecule in a linking reaction specific to a second target nucleic acid, thereby providing a second tagged target nucleic acid. For detection of the second tagged target nucleic acid, the second tagged target nucleic acid can be PCR amplified using universal primers specific to the third and fourth universal DNA segments, where amplicons generated from amplification of the second tagged target nucleic acid form hairpin stems or circles that result in a second detectable signal that is distinguishable from the first detectable signal.

The linking reaction can occur in a first reaction location, and the universal detection step can occur in one or more different reaction locations. The one or more reaction locations of the detection step can include, e.g., a well, a nano-well, a droplet, an array structure, a bead surface, or a flat surface. The one or more reaction locations can include an array structure or a bead surface, where the first universal primer is attached to the array structure or bead surface. Subsequent to the universal segment linking step, and prior to the detection step, a reaction mixture including the product of the linking reaction at the first location is optionally transferred to the one or more different locations, where the reaction mixture is optionally diluted prior to, or during, transfer. In a related aspect, the first and second universal primers are delivered to the one or more different reaction locations prior to, during, or after the linking reaction mixture is transferred to the one or more different reaction locations. Optionally, the one or more different reaction locations of the detection step are disposed within or upon a detection plate or fluidic device, where the first and second universal primers are preloaded into the one or more different reaction locations.

The first universal primer optionally includes a first label proximal to one end of the 5' portion of the first universal primer. The first universal primer can include a polymerase blocking unit disposed between the 5' and 3' portions of the first universal primer. The first label optionally includes a fluorescent dye. The first universal primer can include a label quencher or FRET dye disposed proximal to the same end or proximal to an end opposite the 5' portion of the first universal primer as compared to the first label, where the label quencher or FRET dye is disposed at an effective quenching or FRET distance from the first label. The first detectable signal resulting from hairpin stem or circle formation can include a change of FRET caused by changing the average distance between the first label and the label quencher or FRET dye. Optionally, the label quencher or FRET dye is disposed at a position on the first universal primer selected from: a position between the 5' and 3' portions of the first universal primer, and a position 5' of the junction between the 5' and 3' portions of the first universal primer. Some dyes can generate signal when they are cleaved off from a nucleic acid to which they were attached, and where a label quencher is not required to generate 5' nuclease-based signal, e.g., see U.S. Publication No. 2007/0020664.

Changing the distance between the first label and the label quencher or FRET dye is optionally performed by a mechanism selected from: removal of the label and/or label quencher or FRET dye from the amplicon or primer by a nuclease reaction; increasing the distance between the first label and the label quencher or FRET dye, where the label quencher or FRET dye is initially disposed at an effective quenching or FRET distance from the first label via a double-stranded hairpin stem or a random coil ssDNA structure in the first universal primer, and where the distance between the label quencher or FRET dye and the first label is increased by the intramolecular hairpin dsDNA stem that is formed within the amplicon generated upon extension of the first universal primer; melting of an oligonucleotide from the first universal primer, where the oligonucleotide includes the label quencher or FRET dye, where the first universal primer comprises the first label, and where the hairpin stem or circle generated upon extension of the first universal primer melts the oligonucleotide from the first universal primer, thereby increasing the distance between the label quencher or FRET dye and the first label; and forming a hairpin stem or circle that disposes the first label at an effective FRET distance from a quencher or FRET dye attached to an oligonucleotide that is complementary to the amplicon generated upon extension of the first universal primer.

When changing the distance between the first label and the label quencher or FRET dye is performed by removal of the label and/or label quencher or FRET dye from the amplicon or primer by a nuclease, the first label is optionally disposed between the 3' and 5' portions of the first universal primer, where the label quencher or FRET dye are disposed at the 5' portion of the first universal primer as compared to the first label, where the label quencher is removed from the amplicon with the nuclease, and where the labeled amplicon is detected by capillary electrophoresis or hybridization to a surface-bound oligonucleotide that includes a region complementary to the amplicon.

According to the methods of the present invention, the first detectable signal can be measured at every PCR cycle (e.g., real-time PCR), the first detectable signal can be detected at several points during PCR, and/or the first detectable signal can be detected as an end-point subsequent to PCR (e.g., digital PCR or other end-point detection method). When the first detectable signal is detected as an end-point subsequent to PCR, the method can further include counting the number of wells, nano-wells, droplets, array structures, or beads from which the detectable signal is generated.

When the universal segment linking step is multiplexed such that multiple target nucleic acids of different nucleic acid sequences are tagged with the same or different pairs of universal DNA segments, the multiple target nucleic acids are optionally selected from: a DNA, an RNA, a primate nucleic acid, a rodent nucleic acid, a viral nucleic acid, a bacterial nucleic acid, an archaea nucleic acid, a cDNA, a cDNA corresponding to a short RNA, a genetic variant, a mutation or insertion that confers drug resistance, a somatic mutation, a polymorphism, a single nucleotide polymorphism, a rare allele, a portion of the KRAS gene, a nucleic acid that exhibits a variation in copy number, an intron, an exon, an intron-exon boundary, a splice junction, one or more dinucleotides corresponding to one or more methylated or unmethylated CpG dinucleotides in bisulphite treated DNA, a nucleic acid including one or more restriction enzyme recognition sequences, a portion of human chromosome 21, a portion of the human X chromosome, and a portion of the human Y chromosome, where the presence and/or quantity of the multiple target nucleic acids is detected and combined into a diagnostic output. The diagnostic output is optionally diagnostic for fetal aneuploidy, fetal sex, and/or fetal copy number variation, where the fetal aneuploidy, fetal sex, and/or fetal copy number variation is detected by digitally counting nucleic acid targets indicative of fetal aneuploidy, fetal sex, and/or fetal copy number variation from a maternal blood sample. The nucleic acid targets indicative of fetal aneuploidy, fetal sex, and/or fetal copy number variation can be detected using a first detectable label, and control nucleic acid targets are detected using a second detectable label, where the ratio of digital counts of the labels is used to detect fetal aneuploidy, fetal sex, and/or fetal copy number variation.

Surface-based detection formats are provided by the present invention. For example, the first universal primer can be attached to a surface, where the label is disposed between the 5' and 3' portions of the first universal primer, where the label quencher or FRET dye is disposed at a 5' position relative to the label, where the first or second universal primer is extended by a polymerase where the 5' universal segment with label quencher or FRET dye hybridizes to the amplicon, and where extension of the universal primer removes the quencher or FRET dye from the surface-bound universal segment, thereby resulting or causing a change in the first detectable signal on the surface. According to this embodiment, the second universal primer can be in solution or attached to the surface. Methods other than removal of a quencher by exonuclease activity can be used to generate signal on the surface, e.g., FRET based on molecular beacon, "sunrise primers", duplex between the surface-bound first primer and a separate probe that is disrupted upon primer extension. Signal on the surface can also be measured due to changes in electrochemical properties on the surface due to the first primer extension ("electrochemical detection"), as reviewed in, e.g., Ye and Ju, Sensors (2003) 3:128-145. It will be understood that, in accordance with the present invention, the detection of target nucleic acids can be carried out using electrochemical detection and other non-fluorescence-based detection methods.

When the universal segment linking ("encoding") step is multiplexed such that multiple target nucleic acids of different nucleic acid sequences are tagged with the same or different pairs of universal DNA segments, pools of encoding primers are optionally inventoried or made to order, where the encoding primers are capable of amplifying a nucleic acid target selected from a gene, a portion of a gene, a single nucleotide polymorphism, a nucleic acid target that permits detection of a copy number variation, a methylation target, an miRNA, and a somatic mutation, and where one or more pools of the encoding primers can be provided as a superset. Optionally, the superset includes a first pool of encoding primers capable of amplifying somatic mutations, single nucleotide polymorphisms and/or copy number variants, and where the superset further includes a second pool of encoding primers capable of amplifying one or more cDNAs or miRNAs to determine gene expression levels. Both pools can be used on the same biological sample, where the results of both pools can be combined and analyzed together.

The present invention also provides analyte nucleic acid detection reaction mixtures that include an analyte nucleic acid including a nucleic acid subsequence of interest. The analyte nucleic acid further includes first, second and third tag sequences, the second tag sequence being located between the first and third tag sequences. The mixture also includes a first universal primer comprising a first tag complement subsequence that is complementary to the first tag sequence, a subsequence that includes the second tag sequence, or a subsequence thereof, and a detectable label (e.g., a fluorescent label). The mixture further includes a second universal primer including a sequence that includes the third tag sequence or a subsequence thereof. Optionally, the mixture further includes a complementary nucleic acid that includes subsequences complementary to the nucleic acid subsequence of interest and the first, second and third tag sequences. The nucleic acid subsequence of interest optionally includes a nucleic acid or nucleic acid feature selected from: a DNA, an RNA, a primate nucleic acid, a rodent nucleic acid, a viral nucleic acid, a bacterial nucleic acid, an archaea nucleic acid, a cDNA, a cDNA corresponding to a short RNA, a genetic variant, a mutation or insertion that confers drug resistance, a somatic mutation, a polymorphism, a single nucleotide polymorphism, a rare allele, a portion of the KRAS gene, a nucleic acid that exhibits a variation in copy number, an intron, an exon, an intron-exon boundary, a splice junction, one or more dinucleotides corresponding to one or more methylated or unmethylated CpG dinucleotides, a nucleic acid comprising one or more restriction enzyme recognition sequences, a portion of human chromosome 21, a portion of the human X chromosome, and a portion of the human Y chromosome.

The first universal primer of the reaction mixtures described above optionally includes a label quencher disposed at an effective quenching distance from the label. The label quencher can be located between the first tag complement subsequence and the subsequence that comprises the second tag sequence, where the label is located on an end opposite the subsequence that includes the second tag sequence, as compared to the label quencher.

When the first universal primer includes a label quencher disposed at an effective quenching distance from the label, the label is optionally located between the first tag complement sequence and the subsequence that includes the second tag sequence, where the label quencher is located on an end opposite the subsequence that includes the second tag sequence, as compared to the label. The first universal primer can include a polymerase blocking unit disposed between the first and second universal segments.

The reaction mixtures of the present invention can further include:
a second analyte nucleic acid that includes a second nucleic acid subsequence of interest, the second analyte nucleic acid further including fourth, fifth and sixth tag sequences, the fifth tag sequence being located between the fourth and sixth tag sequences; a third universal primer that includes a second tag complement subsequence complementary to the fourth tag sequence, a subsequence that comprises the fifth tag sequence, or a subsequence thereof, a label and a label quencher, where the label of the second universal label primer is different from the label of the first universal label primer; and, a fourth universal primer including a sequence that includes the sixth tag sequence or a subsequence thereof. Optionally, the sixth tag sequence and the third tag sequence are the same.

The second nucleic acid subsequence of interest optionally includes a nucleic acid or nucleic acid feature selected from: a DNA, an RNA, a primate nucleic acid, a rodent nucleic acid, a viral nucleic acid, a bacterial nucleic acid, an archaea nucleic acid, a cDNA, a cDNA corresponding to a short RNA, a genetic variant, a mutation or insertion that confers drug resistance, a somatic mutation, a polymorphism, a single nucleotide polymorphism, a rare allele, a portion of the KRAS gene, a nucleic acid that exhibits a variation in copy number, an intron, an exon, an intron-exon boundary, a splice junction, one or more dinucleotides corresponding to one or more methylated or unmethylated CpG dinucleotides, a nucleic acid including one or more restriction enzyme recognition sequences, a portion of human chromosome 21, a portion of the human X chromosome, and a portion of the human Y chromosome. Optionally, the first nucleic acid subsequence of interest comprises a cDNA sequence corresponding to an mRNA expressed from a first gene, and the second nucleic acid subsequence of interest comprises a cDNA sequence corresponding to an mRNA expressed from a second gene.

Methods in addition to those described above are provided by the present invention. For example, provided is a method of detecting an analyte nucleic acid, the method including providing a reaction mixture that includes an analyte nucleic acid that includes a nucleic acid subsequence of interest, the analyte nucleic acid further including first, second and third tag sequences, the second tag sequence being located between the first and third tag sequences. The reaction mixture of the method also includes a first universal primer that includes a first tag complement subsequence that is similar (e.g., complementary) to the first tag sequence, a subsequence that includes the second tag sequence, or a subsequence thereof, a label, and a label quencher. The reaction mixture of the method also includes a second universal primer including a sequence that includes the third tag sequence or a subsequence thereof. The second step of the method includes annealing the tag complement subsequence of the first universal primer to the first tag of the analyte nucleic acid. The third step includes performing a first primer extension reaction that extends the first universal primer, where after the extension is complete and dsDNA melts, a hairpin stem forms between first and second portions of the product of the first primer extension reaction, where the first portion includes the second tag sequence, and where the second portion is complementary to the second tag sequence. The fourth step includes annealing the second universal primer to the product of the first primer extension reaction. The fifth step includes performing a second primer extension reaction that extends the universal specificity primer, where the second primer extension reaction releases the label and/or label quencher from the product of the first primer extension reaction. The final step of the method includes detecting the label, where signal from the label indicates the presence of the analyte nucleic acid.

Optionally, the nucleic acid subsequence of interest includes a nucleic acid or nucleic acid feature selected from: a DNA, an RNA, a primate nucleic acid, a rodent nucleic acid, a viral nucleic acid, a bacterial nucleic acid, an archaea nucleic acid, a cDNA, a cDNA corresponding to a short RNA, a genetic variant, a mutation or insertion that confers drug resistance, a somatic mutation, a polymorphism, a single nucleotide polymorphism, a rare allele, a portion of the KRAS gene, a nucleic acid that exhibits a variation in copy number, an intron, an exon, an intron-exon boundary, a splice junction, one or more dinucleotides corresponding to one or more methylated or unmethylated CpG dinucleotides, a nucleic acid comprising one or more restriction enzyme recognition sequences, a portion of human chromosome 21, a portion of the human X chromosome, and a portion of the human Y chromosome.

In one aspect, providing the analyte nucleic acid includes performing a preamplification reaction. According to this aspect, performing the preamplification reaction optionally includes: annealing a first preamplification primer to a target nucleic acid, where the first preamplification primer comprises a 3' portion that anneals to a first portion of the target nucleic acid, and where the first preamplification primer further includes a subsequence complementary (e.g., substantially similar) to the first tag sequence; annealing a second preamplification primer to a complementary strand of the target nucleic acid, where the second preamplification primer includes a 3' portion that anneals to the target nucleic acid, where the second preamplification primer further includes a subsequence that includes the second tag sequence and a subsequence that includes the third tag sequence; and, PCR amplifying the target nucleic acid using the first and second preamplification primers to generate a plurality of amplicons that include the analyte nucleic acid.

Also provided by the present invention is a method to detect or measure the amount of one or more target nucleic acids in a sample by their hybridization to a surface-bound first tailed primer that has a dye and a quencher at a 5' end of the primer, such that when the first tailed primer is extended, a 5' nuclease reaction cleaves off the quencher, generating a change in fluorescent signal on the surface.

The methods and compositions summarized above are described in detail hereinbelow.

DETAILED DESCRIPTION

Overview

Figure 1:
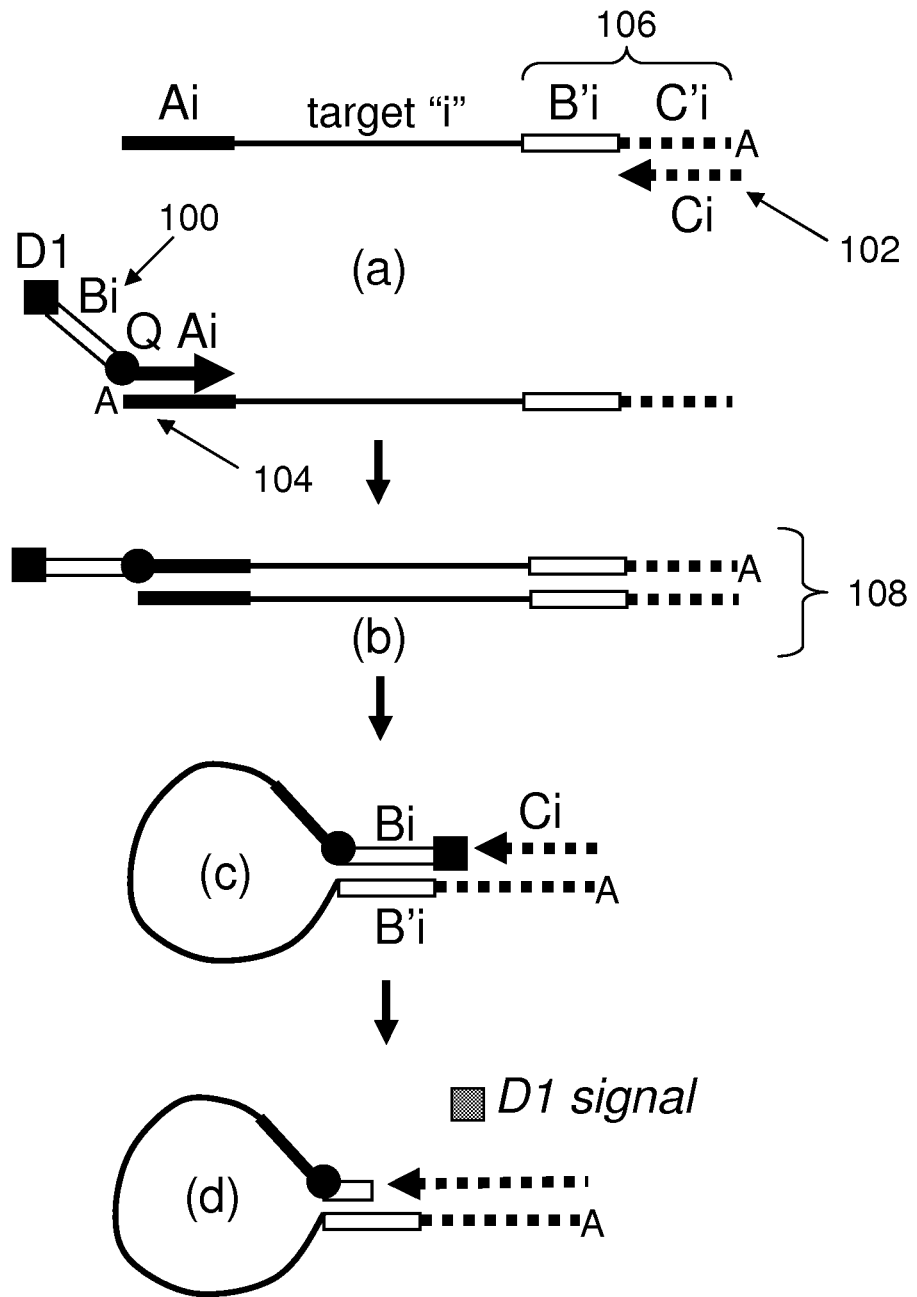
FIG. 1 provides a schematic illustration of an example universal detection format, the format including the formation of a unimolecular hairpin having a stem between universal segments at opposite ends of a first tagged target nucleic acid.

The present invention is broadly applicable to any application in which one desires to detect or measure the amount of one or more target nucleic acids in a sample of interest. Generally, the present invention is directed to methods and compositions for detecting and/or measuring the amount of a target nucleic acid in a sample using a set of universal PCR primers with sequences that do not hybridize to the target nucleic acid of interest. In a preferred aspect, the invention provides a method for detecting a target nucleic acid that includes tagging the target nucleic by linking first and second universal segments at the two ends of a molecule in a way that depends on the target nucleic acid, and PCR amplifying the tagged target nucleic acid using universal primers that hybridize to the universal segments. In this aspect, regions of the PCR amplicons corresponding to the first and second universal segments form intramolecular hairpin stems, which hairpin stem formation is a prerequisite for detection of the nucleic acid, e.g., by removal of a label, label quencher and/or FRET dye from the amplicon. This and other aspects of the invention are described in detail hereinbelow.

This preferred aspect of the invention constitutes a significant improvement over previous nucleic acid detection methods. First, the method provides exceptionally clean results (e.g., clean non-template controls) due to its two-primer and virtual probe (middle universal tag) specificity. Signal is detected only when the three universal segments are present in the tagged target nucleic acid. This is in contrast to prior methods in which signal is generated when only two primers are involved in amplification, e.g., SYBR-green. Second, the detection methods described herein are more cost effective and practical than previous approaches. The universal detection primers need only be made once or can be made in very large batches, because the primers are capable of detecting different target nucleic acids of interest, amortizing their cost over tens, hundreds, thousands or even millions of samples. This feature also makes it practical to achieve higher multiplex detection using more detectable labels/dyes, e.g., one can genotype two [three] SNPs (four [six] alleles) using four [six] distinguishable fluorescent colors in a well. Third, the universal primers can be pre-loaded on a plate (e.g., an integrated fluidic chip), making the method more convenient to use. In accordance with the universal primer detection system of the present invention, pre-loaded universal assays can be provided for detecting any set of targets, e.g., SNPs, genes, chromosomes, cDNAs, copy number variants, miRNAs, methylated/non-methylated regions, and the like. Fourth, the method permits greater variety in terms of "number of assays×number of samples" options for fixed format plates. These and other aspects and advantages of the present invention are set forth in greater detail below.

The present invention provides methods and compositions for detection of nucleic acids that utilizes artificial universal tagging sequences rather than traditional direct detection of DNA/RNA using primers and probes matching the target nucleic acids. Target nucleic acids are only used to specifically connect distinct universal tagging sequences into a single molecule during the first encoding step. The detection is based on the intramolecular Watson-Crick base-pairing (a hairpin stem) between the two universal tags in the amplicon. The base-pairing between the two universal tagging sequences enables detection of nucleic acids that preserves "three tag" detection specificity: spurious amplifications and primer dimers have a low probability of forming hairpins. Also provided is universal surface solid-phase detection for encoded nucleic acid targets.

Exemplary Universal Detection Formats

A variety of universal detection formats are provided by the present invention. A first example format is schematically illustrated in FIG. 1. As shown, step (a) includes priming on both strands of a first tagged nucleic acid using first universal primer 100 and second universal primer 102. A 3' portion (Ai) of the first universal primer anneals to first universal segment 104, while a 3' portion (Ci) of the second universal primer anneals to portion C'i of second universal segment 106. The first universal primer includes detectable label D1 at or near the 5' end of the first universal primer, 5' portion (Bi) and a label quencher or FRET dye (Q). Optionally positioned proximal to the label quencher or FRET dye is a polymerase blocking unit, e.g., HEG (hexethylene glycol), THF (tetrahydrofuran), or any other blocker known in the field in case the presence of the quencher or FRET dye is not sufficient to stop the polymerase extension. For example, primers with a HEG or Sp-18 polymerase blocking unit are commercially available, e.g., from BioSearch Technologies. For the sake of simplifying the figures herein, polymerase blocking units are not shown. However, it will be understood that a polymerase blocking unit is optionally positioned in close proximity to quencher "Q" in the middle portion of the universal primers. A polymerase blocker may not be required if the 5'-tail that folds into a stem has one or more bases at the 5' end that are not complementary to the middle universal tag sequence, so that the hairpin formed by the opposite strand of DNA (with the 3'-end at the end of the stem) is not extendable during PCR. One can also design a small hairpin into the 5' portion of the primer 100, so that the dye and the quencher are brought closer together, similar to "Sunrise" primers and probes to improve quenching and decrease background fluorescence. For example, see U.S. Pat. Nos. 5,866,336 and 6,270,967.

PCR amplification results in double stranded product 108. In this example, a polymerase blocking unit positioned proximal to the label quencher or FRET dye prevents a polymerase from copying the 5' portion (Bi) of the first universal primer, such that the bottom strand of product 108 cannot form a hairpin when it becomes single-stranded. Formation of such a hairpin would result in the 3' end of the stem annealing to the amplicon such that polymerase extension of this 3' end would terminate the PCR reaction.

Hairpin formation is shown at step (c) of FIG. 1. Product 108 is melted (e.g., by raising the temperature to approximately 95° C.) to separate the upper strand from the lower strand, and when the temperature is subsequently decreased, the upper strand of product 108 forms a hairpin having a stem between 5' portion (Bi) of the first universal primer and portion B'i at the opposite end of the strand. Also at step (c), the second universal primer anneals to a complementary portion of the upper strand. Intra-molecular hairpin formation occurs rapidly and is driven by thermodynamics: the free energy is determined by stem length, GC-content and loop length. It is important that the melting temperature (Tm) of the hairpin be significantly higher (e.g., approximately 10° C. or higher) than the Tm of the second universal primer 102. This way, when the temperature is decreased, nearly 100% of the molecules will form the hairpin before the second universal primer anneals and is extended. Upon extension of the second universal primer at step (d), 5' nuclease activity of the polymerase cleaves the detectable label D1 from the 5' end of the amplicon, thereby increasing the distance between the label and the quencher or FRET dye and permitting detection of the label. A wide variety fluorescent dyes are known in the art and commercially available, e.g., FAM, TET, JOE, VIC, HEX, CY3, TAMRA, TexasRed, CY5, ROX and many other dyes and quenchers can be used, e.g., MGB-NFQ, BHQ-[0123], ZEN quencher from IDT.

The present invention provides approaches for signal generation subsequent to hairpin formation in addition to 5' nuclease activity. Alternative methods previously described include "molecular beacons"-type detection, which does not require 5' exonuclease activity. Rather, a fluorescent signal is generated when the hairpin forms, increasing the spatial distance between the dye and the quencher, thereby decreasing quenching and increasing the fluorescent signal. For a comparison between scorpion "molecular beacon", scorpion 5' nuclease and bimolecular 5' nuclease (TAQMAN™ probe) detection methods, see Thelwell et al., Nucleic Acids Research (2000) 28(19): 3752-61.

Because the 5' Bi tails of the detection primers in FIG. 1 are not copied during PCR, they can contain any modified bases that are known in the art. These may include, PNA and LNA, which make dsDNA more stable and thus enable shorter hairpin stems. If these are used at the very 5' end of the Bi primers, they will make the probes resistant to the 5' nuclease cleavage, thus permitting the use of polymerases with the exonuclease activity and generating the molecular beacons-type ("probe stretching") signal described above. Similarly, 2-amino-adenosine is known to increase the stability of the T-A pairs, again permitting shortening of the stems. RNA bases in the Bi parts will lead to the RNA-DNA hairpin stems that are more stable than DNA-DNA. ZEN quencher from IDT also stabilizes dsDNA enabling shortening of stems. In addition, uridines, THF, oxo-G and other enzymatically cleavable bases (e.g., UDG, EndoV, Fpg, etc.) can be used to measure the 100% primer digestion signal after the detection PCR. This signal can be compared with the end-point detection signal and serve as a positive control.

Modified bases that can be copied by polymerases can be used in the Ai parts and in the Ci primers (referring to FIG. 1), e.g., 2-amino-adenosine can stabilize priming. These modified bases usually have a weaker affinity to the polymerases and thus can decrease the likelihood of primer dimer formation (e.g., as described in U.S. Pat. No. 6,794,142). The modified bases increase the cost of the universal primers, but because primers are amortized over hundreds of thousands or even millions of samples, the increase per sample is negligible. The modified bases described above are well known in the art, e.g., Glen Research catalog website or TriLink Biotechnologies product website offers a broad range of modified bases.

Figure 2:
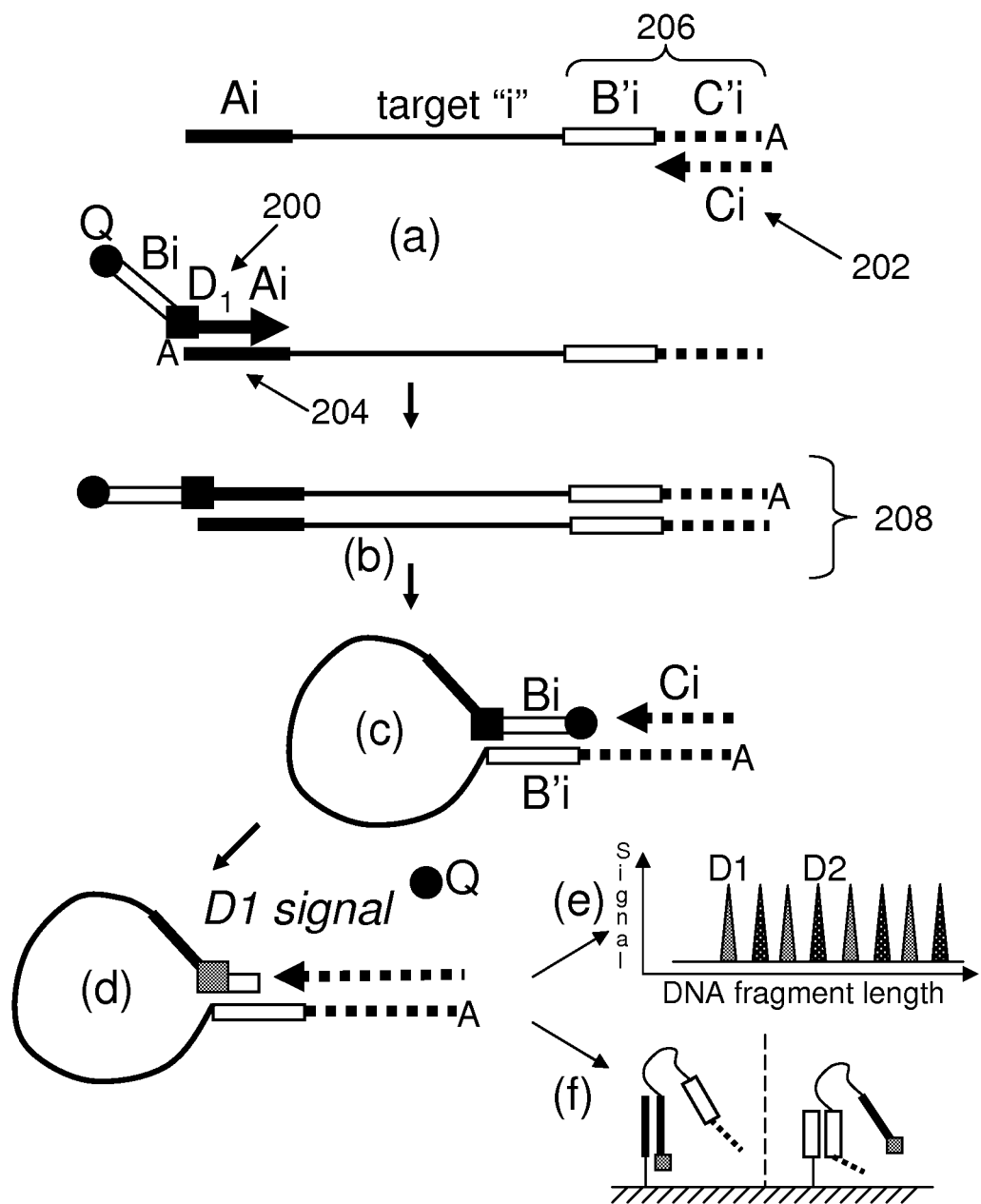
FIG. 2 provides a schematic illustration of an example universal detection format similar to that shown in FIG. 1, but where the positions of the detectable label and label quencher are switched, e.g., so that labeled amplicons can be detected by capillary electrophoresis (CE) or surface hybridization.

The present invention also provides a detection scheme similar to that shown in FIG. 1, but where the positions of the detectable label and quencher or FRET dye on the first universal primer are switched. This embodiment, which is particularly useful for applications where retention of the detectable label on the amplicon is desirable, is schematically illustrated in FIG. 2. As shown, step (a) includes priming on both strands of a first tagged nucleic acid using first universal primer 200 and second universal primer 202. A 3' portion (Ai) of the first universal primer anneals to first universal segment 204, while a 3' portion (Ci) of the second universal primer anneals to portion C'i of second universal segment 206. The first universal primer includes a label quencher or FRET dye (Q) at or near the 5' end of the first universal primer, 5' portion (Bi), and detectable label D1. PCR amplification results in double stranded product 208. Universal hairpin formation is shown at step (c). Upper strand of product 208 forms a hairpin having a stem between 5' portion (Bi) of the first universal primer and portion B'i at the opposite end of the strand. Upon extension of the second universal primer at step (d), 5' nuclease activity of the polymerase cleaves the quencher or FRET dye from the 5' end of the amplicon, thereby increasing the distance between the quencher or FRET dye and the label and permitting detection of the label. In this example, a polymerase blocking unit is positioned proximal to label D1, so that the label is not cleaved from the amplicon.

When practicing the "switched" format in which the detectable label is a fluorescent dye disposed at an internal portion of the first universal primer, it is preferable that the number of guanine ("G") bases in the immediate vicinity of the detectable label be minimized or avoided altogether. This is because guanine is capable of quenching fluorescence emitted from certain fluorophores, potentially reducing the strength of the detected signal from the label.

Retaining the detectable label on the amplicon can be useful in a number of applications, e.g., when it is desirable to detect the amplicon via capillary electrophoresis (CE), or on a surface or bead (e.g., in the case of surface- or bead-based DNA arrays). Step (e) of FIG. 2 schematically illustrates capillary electrophoresis (CE) detecting peaks at certain amplicon lengths. Step (f) schematically illustrates a target-specific DNA array, where the labeled amplicon generated at step (d) hybridizes to complementary nucleic acids attached to the array surface, permitting detection of the amplicon as color or signal on the array. The complementary nucleic acids attached to the array surface can be universal as shown in FIG. 2(f) or target-specific.

Both CE and DNA arrays allow high multiplex endpoint detection of labeled amplicons. For example, amplicons generated using the "switched" format with size ranges between, e.g., 70 and 200 bases, can be detected as fluorescent CE peaks in four or more dyes. Assuming that robust peak separation requires approximately 10 bases between peaks in the same color, it is possible to detect, e.g., 4 dyes×(200−70)/10=52 peaks corresponding to 26 biallelic SNPs, or detecting the presence or absence of 52 DNA targets. DNA arrays have essentially unlimited detection multiplicity.

The "switched" format can be used for a combined screening/identification in cases where the majority of samples are expected to be negative. For example, in a diagnostic or epidemiological application, one can detect the presence of any of 52 different pathogens or 52 alleles using real-time (or end-point in a well) PCR detection. The majority of samples are expected to be negative, but if one of the dyes shows signal in a qPCR well for a given sample, the products of this amplification can be loaded onto a CE lane or DNA array. The exact nature of the pathogen or alleles can be determined based upon the size of the DNA fragment on CE, or known DNA sequence spotted at a specific location on the array.

Figure 3:
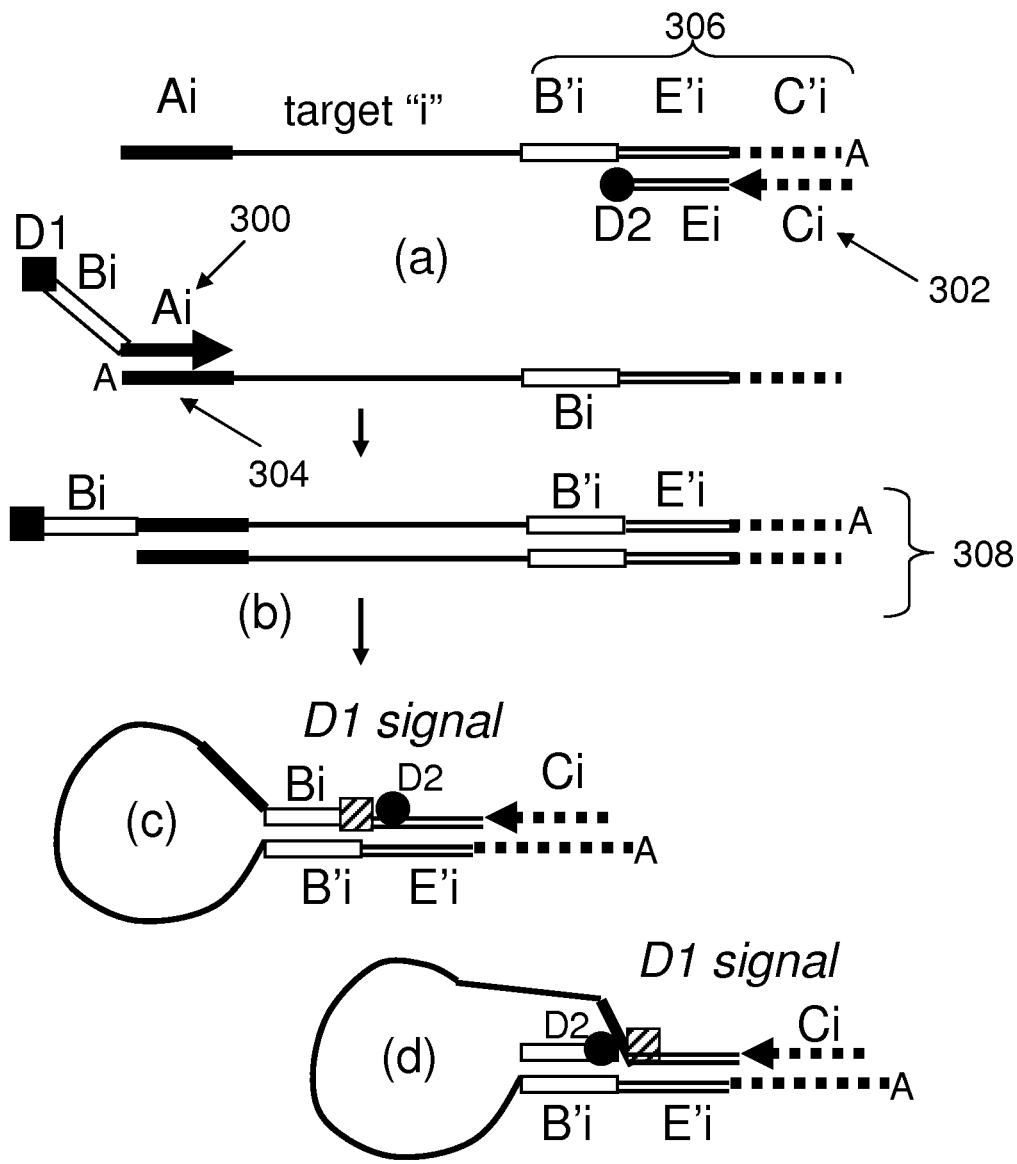
FIG. 3 schematically illustrates an example universal detection format that utilizes fluorescence (or Forster) resonance energy transfer.

A third universal detection format, which utilizes fluorescence energy resonance transfer (FRET) to generate a detectable signal (or a change in detectable signal), is schematically illustrated in FIG. 3. FRET can be useful to expand the number of detectable fluorescent colors with longer (red) wavelengths. As shown, step (a) includes priming on both strands of a first tagged nucleic acid using first universal primer 300 and second universal primer 302. A 3' portion (Ai) of the first universal primer anneals to first universal segment 304, while a 3' portion (Ci) of the second universal primer anneals to portion C'i of second universal segment 306. The first universal primer includes a dye (D1) disposed at or near the 5' end of the primer, but does not include a quencher. D1 does not generate signal, because the light in the instrument does not excite the D1 dye. In addition, there is a separate probe molecule with a dye (D2) that is excited by the light in the instrument. PCR amplification results in double stranded product 308.

During the detection reaction shown at step (c) of FIG. 3, a hairpin forms and the probe molecule having dye D2 anneals to portion E'i of the amplicon, such that dyes D1 from the stem and D2 from the probe molecule come into close proximity to each other. D2 emits light shifted to the red (longer wavelength) and excites D1, resulting in the generation of a detectable FRET signal. It is important that the probe molecule have a higher melting temperature than the second universal primer, in order to provide sufficient time to detect/measure the FRET signal before the second universal primer extends.

The detection reaction shown at step (d) of FIG. 3 is a variation of that shown at step (c). In particular, the first universal primer can have dye D1 disposed between sub-segments Ai and Bi, and the probe molecule having dye D2 anneals to portion B'i of the amplicon. Annealing of the probe molecule brings dyes D1 and D2 into close proximity to each other, resulting in the generation of a detectable FRET signal.

In one aspect, polymerases without exonuclease activity, but with strand-displacing activity, are used for the FRET detection. Alternatively, polymerases with 5' exonuclease activity and strand-displacement activity can be used, but preferably when the probe is resistant to nuclease digestion. For example, PNA, LNA or other modifications can be used to confer resistance by the probe molecules to nuclease digestion. The present invention also provides FRET and 5' nuclease detection in the same well. According to this embodiment, as the temperature is decreased from the denaturation temperature (e.g., 95° C.) during PCR, the FRET signals due to their thermodynamic/temporal nature are measured first, and the signal generated from 5' nuclease is measured second.

Figure 4:
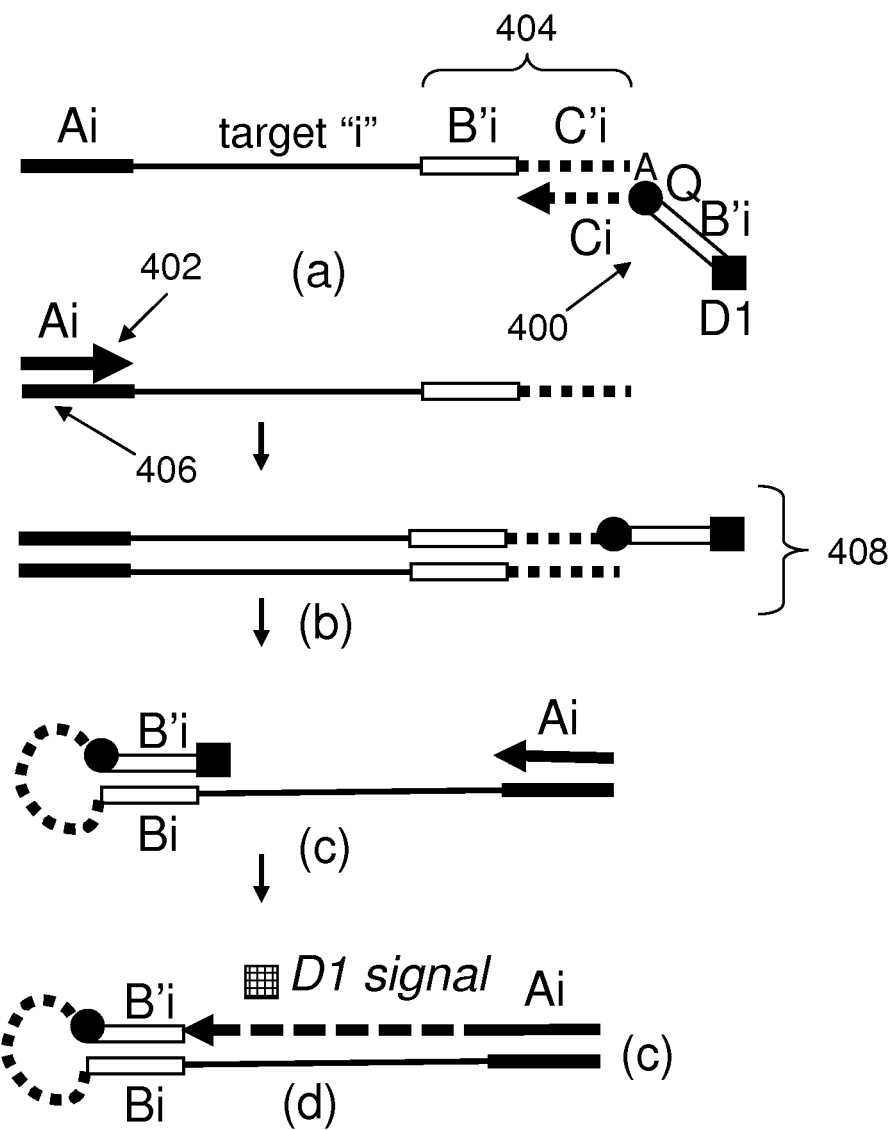
FIG. 4 provides a schematic illustration of an example universal detection format, the format including the formation of a unimolecular hairpin having a stem between complementary subsequences present in a single universal segment at one end of a first tagged target nucleic acid.

FIG. 4 schematically illustrates a fourth example detection format in which a hairpin step forms between complementary regions on the same side of the first tagged target nucleic acid. The tagged target nucleic acid is amplified using first universal primer 400 (including D1-B'i-Q-Ci-3') and second universal primer 402 (including Ai). D1 is a detectable label and Q is a quencher and polymerase blocker. A 3' portion (Ci) of the first universal primer anneals to first universal segment 404, while a 3' portion (Ai) of the second universal primer anneals to second universal segment 406. PCR amplification results in double stranded product 408. After product 408 is melted and the temperature is decreased, a hairpin forms with the stem between Bi and B'i. A signal is generated by the 5' nuclease activity of a polymerase as it extends primer Ai.

Figure 5:
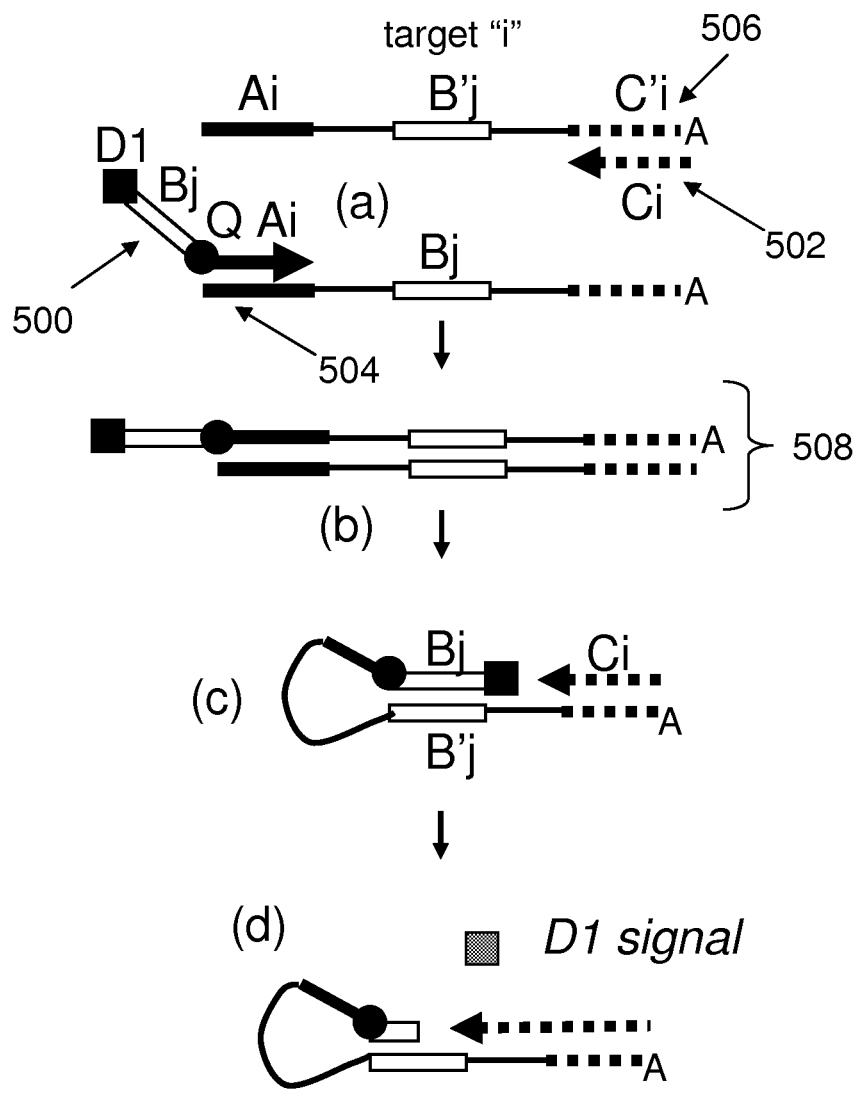
FIG. 5 schematically illustrates an example universal detection format, the format including the formation of a unimolecular hairpin having a stem between a portion of a first universal segment and a sequence corresponding to the target nucleic acid of interest.

The present invention also provides detection formats where a subsequence of one of the universal detection primers forms a hairpin stem with a sequence corresponding to the target nucleic acid. This format is schematically illustrated in FIG. 5. As shown, the tagged target nucleic acid is amplified using first universal primer 500 (including D1-Bj-Q-Ai-3') and second universal primer 502 (including Ci). D1 is a detectable label and Q is a quencher optionally associated with a polymerase blocker. A 3' portion (Ai) of the first universal primer anneals to first universal segment 504, while a 3' portion (Ci) of the second universal primer anneals to second universal segment 506. PCR amplification results in double stranded product 508. After product 508 is melted and the temperature is decreased, a hairpin forms with the stem between Bj and B'j, where B'j is a sequence corresponding to the target nucleic acid. In this example, a signal is generated by removal of the label from the amplicon by the 5' nuclease activity of a polymerase as it extends primer Ci.

Figure 6:
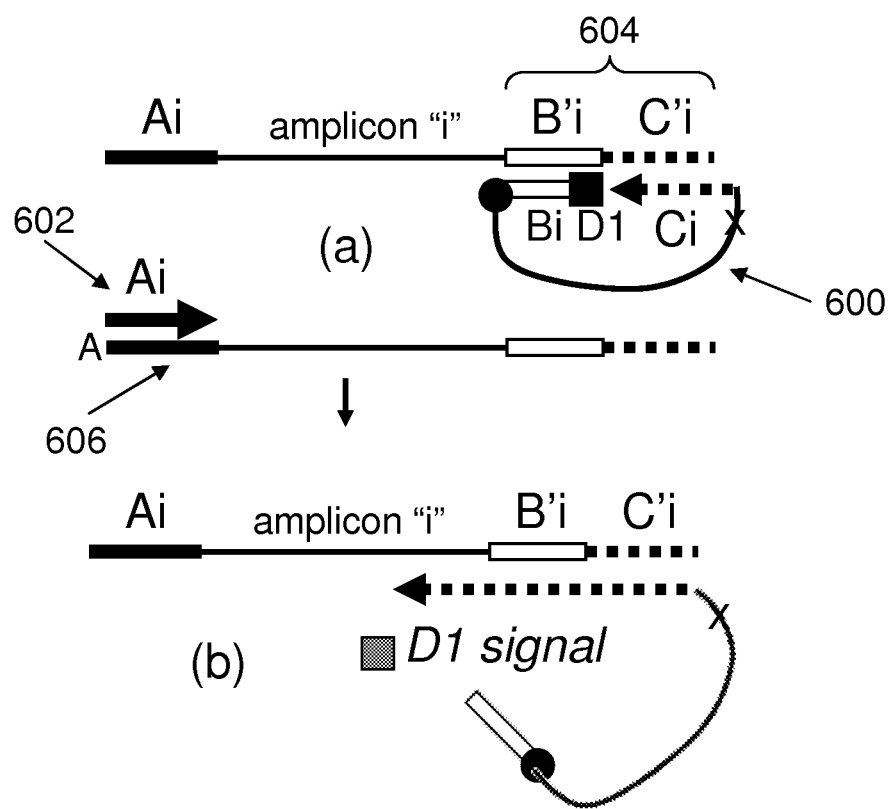
FIG. 6 schematically illustrates an example universal circle detection format.

A further example detection format involving the formation of a universal circle is schematically illustrated in FIG. 6. The tagged target nucleic acid is amplified using universal primer 600 (including D1-Bi-Q-spacer-x-Ci-3') and second universal primer 602 (including Ai), where D1 is a detectable label, Q is a quencher and "x" is a polymerase blocking unit. A 3' portion (Ci) of the first universal primer anneals to first universal segment 604, while a 3' portion (Ai) of the second universal primer anneals to second universal segment 606. In this example, extension of the first universal primer at step (b) generates a signal by 5' exonuclease cleavage of D1 and separation of D1 from the quencher.

As will be appreciated, the universal detection methods provided by the present invention include surface-based detection formats. Surfaces upon which detection can occur include the surface of a well (e.g., a nano-well), an array structure (e.g., a reaction region on an array), a bead surface, and the like. One example of surface-based detection provided by the present invention is universal detection by emulsion PCR (ePCR). Emulsion PCR is known in the art and involves the isolation of DNA molecules along with primer-coated beads in aqueous droplets within an oil phase.

Figure 7:
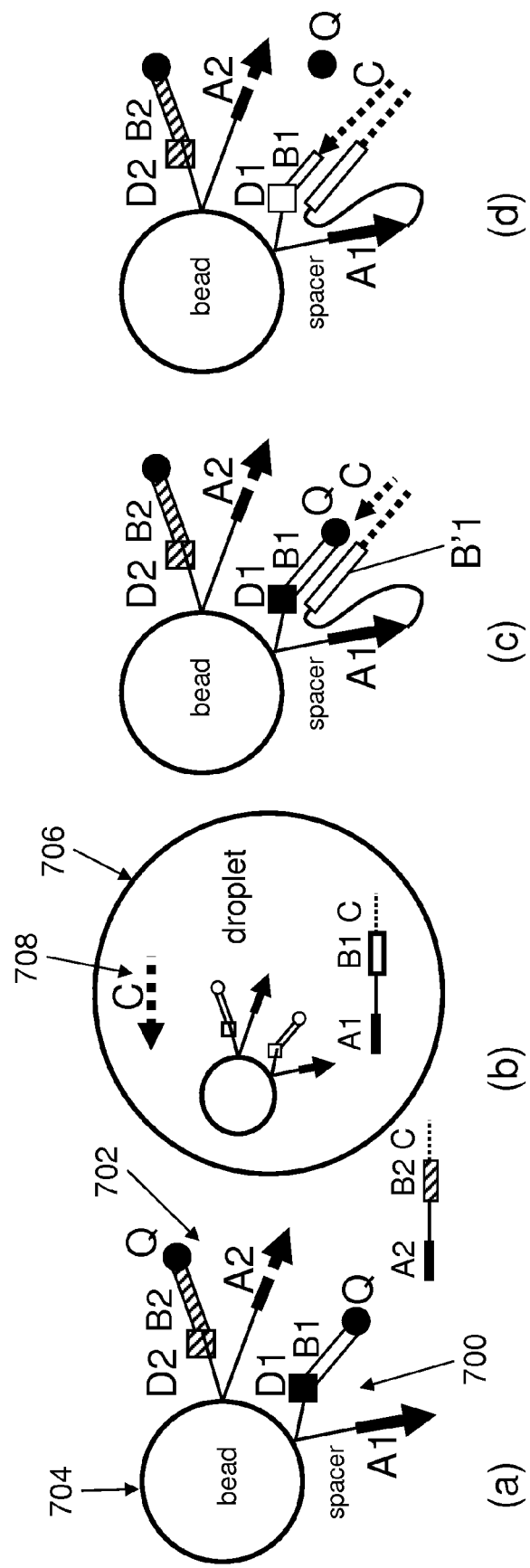
FIG. 7 provides a schematic illustration of an example surface-based universal detection format that utilizes emulsion PCR.

An example of universal detection by emulsion PCR is schematically illustrated in FIG. 7. As shown, first universal primer 700 and second universal primer 702 are attached to bead 704. The first universal primer includes Q-B1-D1-spacer-[surface]-spacer-A1-3' and the second universal primer includes Q-B2-D2-spacer-[surface]-spacer-A2-3', where D1 and D2 are detectable labels (e.g., fluorescent dyes) and Q is a label quencher. The ePCR micro-reactor (droplet 706) has a bead and zero or one or more of each tagged target nucleic acid molecules for each color, e.g., tagged target nucleic acid A1-B1-C is shown inside the droplet, while A2-B2-C is outside the droplet. Third universal primer 708 (including C) and PCR reagents are inside the droplet. As shown at (c), during ePCR, the A1-bead primer extends and portion B1 of the first universal primer anneals to B'1 of the extended primer. As shown at (d), when the third universal primer (C) extends, quencher Q is cleaved off, D1 becomes unquenched, and D2 remains quenched. D1 and/or D2 signal indicates if one (or both) tagged target nucleic acids were present in the droplet.

Universal primers of the present invention can be attached, e.g., to a bead surface or a flat surface. The dyes are quenched, but when the surface-bound primers are involved in PCR, the 5' nuclease reaction cleaves off the quencher and generates detectable signal. The primers can be attached to the beads using standard methods known in the art, e.g., primary amino groups binding to slides with activated carboxyl groups. For example internal Amino Modifier C6-dT or UNI-LINK™ modified bases can be used to attach the first universal primers to the surface. The total number of attached primers depends on the bead size. Smaller beads, e.g., approximately 1 micron beads can accommodate hundreds of thousands of primers. Long spacers, e.g., several Ts or any other random DNA sequences, or so called "spacers", e.g., spacer 9, spacer 12 (Integrated DNA Technologies catalog website, "Modifications") can be used so that both 3' and 5' ends of primers are far enough from the surface to participate in the PCR extension and 5' nuclease reactions, respectively (e.g., see FIG. 7(a)). An ePCR reaction is prepared by mixing the appropriate number of beads and volumes of oil, surfactants, etc. and PCR master mix that includes the second universal primer (e.g., primer 708 in FIG. 7) and the tagged DNA with universal ends (e.g., FIG. 7(b)). Further details regarding the attachment of various reaction components, e.g., primers, probes, templates, and the like, are described, e.g. in Mitterer G., Schmidt W. M. (2006) Methods Mol. Biol, 345: 37-51; Fedurco M. et al (2006) Nucleic Acids Res., 34: e22; Kojima T. et al (2005) Nucleic Acids Res., 33: e150; Mercier J. F., Slater G. W. (2005) Biophys. J., 89: 32-42; Mercier J. F. et al (2003) Biophys. J., 85: 2075-2086.

For digital PCR, each ePCR micro-reactor (e.g., droplet, FIG. 7(b)) with a bead has on average less than one copy of the pre-amplified target molecule for each detection color, so that only a subset of beads will generate signal in each color and each bead can have signals in more than one color. During ePCR, a single pre-amplification molecule exponentially amplifies, e.g., A1-B1-C at FIG. 7(b), driving approximately $10^5$ or more A1-bead primer extensions (e.g., see FIG. 7(c)), and the 5' nuclease reaction cleaves off the 5' quencher (see FIG. 14(d)). Because the A2-B2-C pre-amplification target was outside of the droplet (FIG. 14(b)), the bead will have no detectable D2 signal.

After ePCR, the emulsion is broken, the beads are deposited on the slide surface (or, e.g., 454 PicoTiter Plates), and beads in each color or no signal are counted. For example, two colors are shown in FIG. 7, but four colors can be routinely detected in existing instruments, e.g., SOLID™/ 454. This can be done, e.g., using a microscope with a CCD. A straightforward statistical analysis of the ratios of bead counts with color and no signal, and between the different colors, will yield very accurate relative counts for the number of the tagged molecules. Each detection color can correspond to one or several pre-amplification targets that are counted together. For example, in the case of trisomy 21 detection (e.g, see FIGS. 23 and 24) several chromosome 21 targets are detected using D1/color 1, autosomal non-chromosome 21 targets use D2/color 2, X-chromosome targets use D3/color 3, and so on.

Similarly, digital counts can be obtained using bridge cluster amplification on the surface with densely attached universal detection primers, e.g., see FIGS. 8 and 9 and the accompanying description below). For example, the cBot Cluster Generation System from Illumina can be used to generate isothermal bridge amplification clusters. Alternatively, bridge PCR cycling can be used. Similar to the beads approach described above, each cluster is clonal and originates from a single ssDNA pre-amplified molecule that randomly binds to the A1-3' or A2-3' on the slide surface (FIG. 7(a)) for the first extension cycle. Bridge amplification gives two options in terms of color detection: a plain "C" universal primer is "densely" attached to the surface so that it is involved in "bridge amplification" with any of the labeled universal primers, generating cluster signal in the color that corresponds to the specific pre-amplification target. Alternatively, bridge amplification can use two labeled primers based on the two-strand universal detection (e.g., see FIG. 18 below), so that each cluster gives a two-color signal. The latter approach can detect more targets as compared to single color detection. For example, four universal primers labeled in four colors can detect six different targets: 4*3/2=6, all possible 2-color combination of 4 colors. Five-color detection will have the ability to detect 5*4/2=10 tagged products.

Commercially available sequencing instruments, e.g., from Illumina (e.g., HiSeq 1000/2000, GAIIx or MiSeq instruments) can be used to read the detectable signal on slides. The number of clusters in each color (or a pair of colors) is counted, and the numbers indicate how many pre-amplified target molecules were present in the sample.

Figure 18:
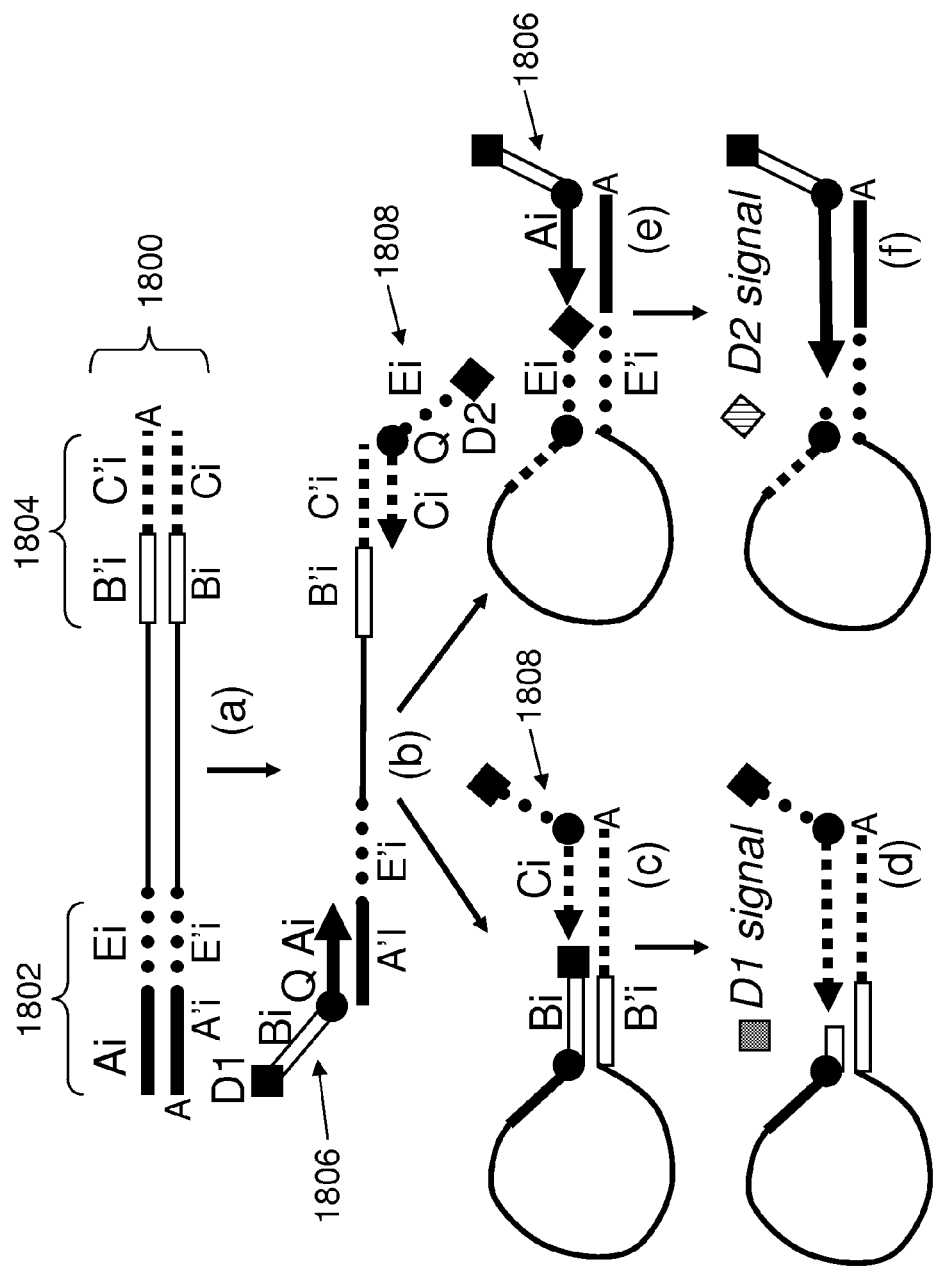
FIG. 18 schematically illustrates an example universal two-strand detection application.

It should be noted that bridge amplification or bridge PCR can be performed on beads in addition to flat surface. In this embodiment, the amplification is similar to ePCR, except instead of the universal primer "C" in solution (as in FIG. 7(b)), the "C" primer is attached to the beads. This "bridge on the bead" approach has the benefit of a significantly stronger signal, e.g., SOLID™ 1 micron beads have approximately 100,000 extended molecules versus approximately 1,000 in a bridge amplification cluster. This is because a single tagged DNA molecule can start multiple clonal clusters on the bead surface in an ePCR droplet. This method also allows several types of beads with different labeled universal primers to be implemented. At the same time, the "bridge on the bead" method has features from the bridge amplification, e.g., it permits two-strand (two color) universal detection (e.g., as generally shown in FIG. 18).

Figure 8:
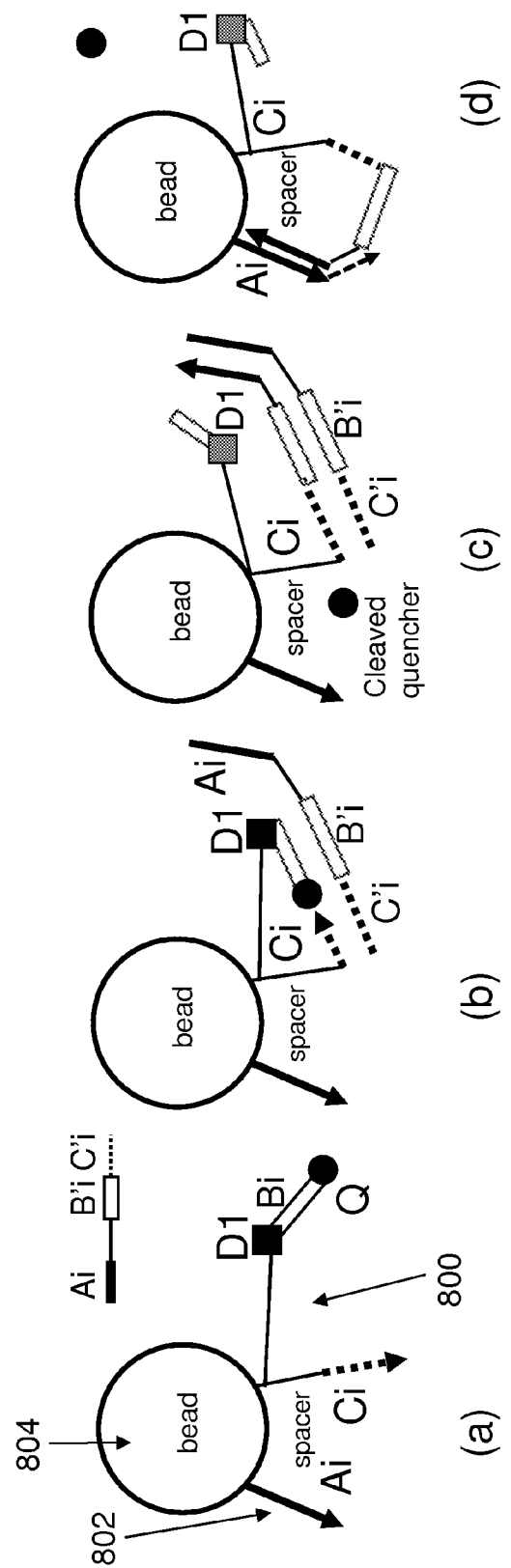
FIG. 8 schematically illustrates an exemplary surface-based universal detection format that utilizes bridge PCR.

Another surface-based universal detection format provided by the present invention is schematically illustrated in FIG. 8. In this example, universal detection is accomplished via "bridge PCR" or bridge amplification, where the universal primers are attached to the surface of a bead. As shown, first universal primer 800 and second universal primer 802 are attached to the surface of bead 804. The first universal primer includes Q-Bi-D1-spacer-[surface]-spacer-Ci-3' and the second universal primer includes Ai, where Q is a label quencher and D1 is a detectable label, e.g., a fluorescent dye. First tagged target nucleic acid (including Ai-B'i-C'i) anneals to both the Bi and Ci portions of the first universal primer, bringing the 3'-end of Ci close to the 5'-quencher of Bi. The extension of Ci at step (c) cleaves the quencher and generates fluorescent signal D1. At step (d), the extended amplicon forms a bridge by looping back onto Ai on the surface, and Ai extends to form a complementary strand, thus continuing amplification on the surface. The first universal primer on the surface is shown attached in the middle. An alternative configuration in accordance with the present invention would be to have a spacer-Ci-3' primer attached to the bead at the 5' end and Q-Bi-D1-spacer-5' attached at the 5' end. The ends of the two attached primers would come into proximity with each other due to their attachment to the same bead surface. In this example, the two parts of the first universal primer are formally two separate oligos, but being bound to the same bead surface they are effectively linked into a single molecule where the surface provides a link.

Figure 9:
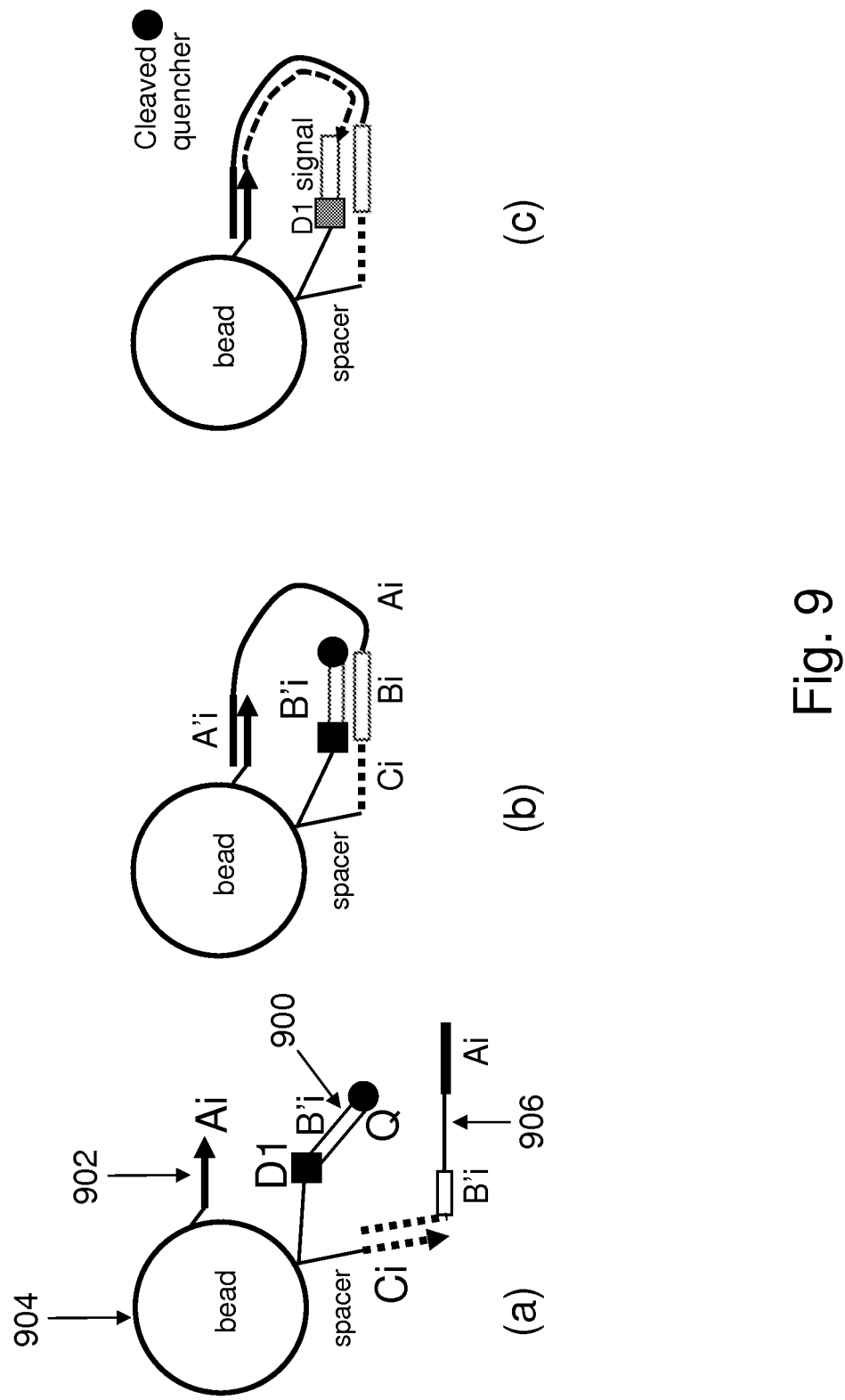
FIG. 9 provides a schematic illustration of a second surface-based universal detection format that utilizes bridge PCR.

Universal detection via bridge PCR can also be accomplished as schematically illustrated in FIG. 9. As shown, first universal primer 900 and second universal primer 902 are attached to bead 904. The first universal primer includes Q-B'i-D1-spacer-[surface]-spacer-Ci-3' and the second universal primer includes spacer-Ai-3'. First tagged target nucleic acid 906 (Ai-B'i-C'i) anneals to the Ci portion of the first universal primer. At step (b), extension of Ci attaches the complement of the first tagged target nucleic acid to the surface. The extension product (amplicon Ci-Bi-A'i-3') anneals to both B'i and the Ai portion of the second universal primer on the surface. The extension of Ai at step (c) causes 5' nuclease cleavage of the quencher, permitting detection of a fluorescent signal emanating from dye D1. The spacers attached to the surface are preferably long and flexible/rotatable.

Multiple beads with different intrinsic bead properties can be used for multiplex detection in FIGS. 8 and 9. For example, bead color (Luminex microspheres), holographic images (Illumina VERACODE™) or barcodes (Applied BIOCODE™ beads, Affymetrix liquid arrays) can be pooled together for the detection step. One can decode both the universal tags "i" on each bead that encode each target based on the intrinsic bead properties and the surface signal generated by the label on the first universal primer that measures the amount of the tagged target nucleic acid in the sample.

Surface detection for multiplex targets requires attaching universal primers to beads or surfaces (FIGS. 8a, 9a). Bead encoding can be performed by the bead vendor: each type of bead with different colors or barcodes is combined with specific tags Ai, Bi, Ci. All encoded beads are pooled together for multiplex detection and the universal pool can be used to detect or measure any nucleic acid target. Users can mix their samples containing target nucleic acids, encoding primers, master mix and encoded beads and PCR cycle the mixture. First, encoded target molecules will be generated and then these molecules anneal to the surface bound universal primers and generate a signal on the surface (see, e.g., FIGS. 8 and 9). In the alternative two-step detection method, targets are first tagged by linking universal segments together. The tagged/encoded sample is optionally diluted and added to the pooled decoding beads for detection. After hybridization to the beads, bridge amplification or PCR generates signal on the bead surface. For the readout, the beads can be laid on the surface (e.g., VERACODE™), streamed past a detector (e.g., Luminex microspheres) or directly imaged in a well (e.g., Applied BIOCODE™). The barcode on a bead or color of a microsphere determines the target and the fluorescent signal on the surface measures the amount of this nucleic acid target in the sample. Thus, as provided by the present invention, multiplex surface detection can measure the amounts of multiple targets in a well using a set of universal beads or microspheres.

It will be appreciated that the universal detection formats described above are exemplary approaches. Additional universal detection formats are possible and within the scope of the present invention. It will also be appreciated that any of the exemplary universal detection formats described above can be combined with any of the universal segment linking strategies and universal detection applications described herein. Further, it will be understood that the universal detection formats of the present invention can occur in multiplex, where 2 or more, e.g., 4 or more, 6 or more, 8 or more, 10 or more, hundreds or more, or even thousands or more different target nucleic acids of interest can be detected simultaneously in wells (e.g., nano-wells), on beads, on an array, using integrated fluidics chips (IFC), and the like.

Exemplary Universal Segment Linking Strategies

The above section entitled "Exemplary Universal Detection Formats" describes universal detection approaches that utilize a first tagged target nucleic acid of interest. The present section describes exemplary strategies for linking first and second universal DNA segments into a single molecule in a linking reaction dependent on a first target nucleic acid of interest, thereby providing the first tagged target nucleic acid. It will be appreciated that multiple different target nucleic acids can be "encoded" with different pairs of universal segments, such that the target nucleic acids can be differentially detected (e.g., using any of the universal detection formats described above) based upon the particular pair of universal segments associated with each different target nucleic acid.

Figure 10:
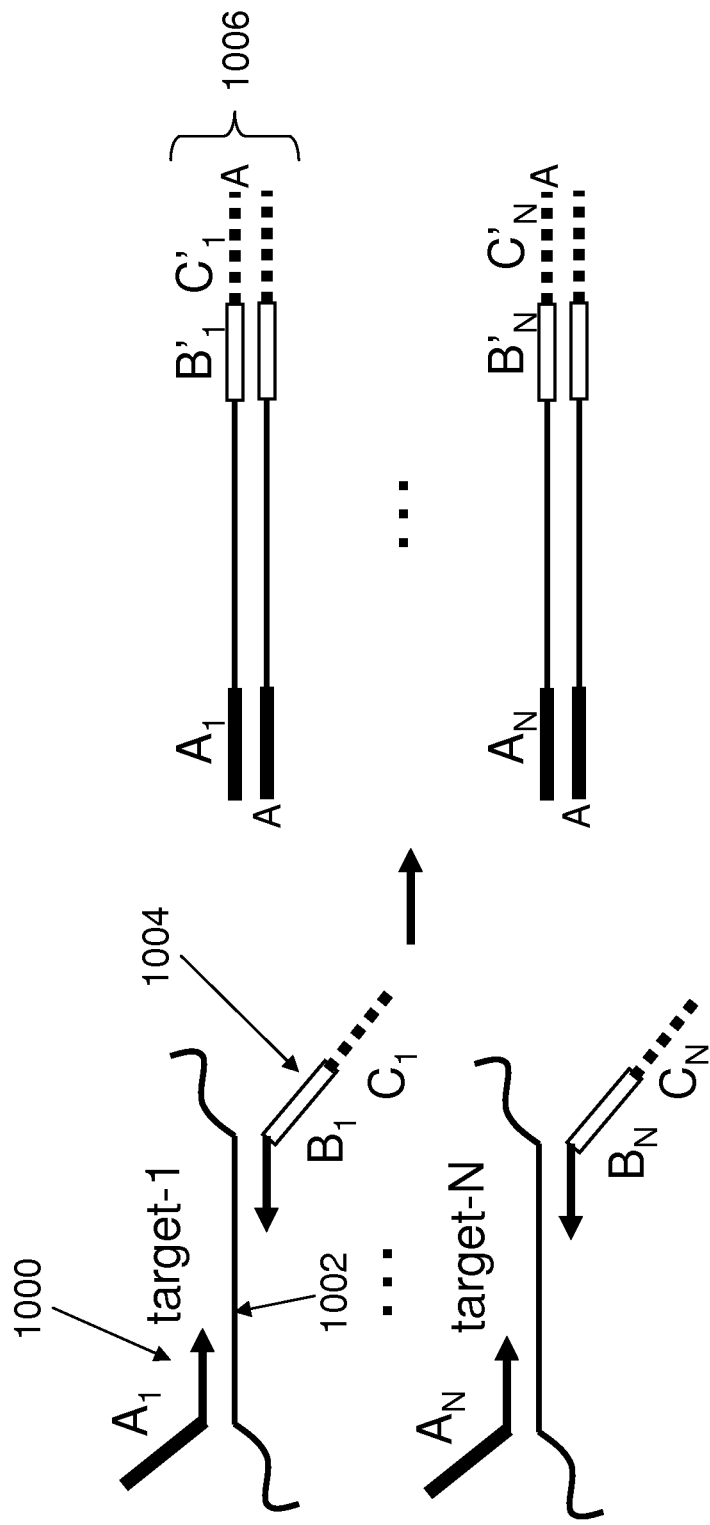
FIG. 10 schematically illustrates a universal segment linking strategy that includes preamplification of a target nucleic acid with primers having 3' ends specific to the target nucleic acid and 5' ends having universal segments.

A first exemplary universal segment linking strategy involves "preamplification" of the target nucleic acid of interest with PCR primers that include a 3' portion specific to the target nucleic acid and a 5' universal segment. Linking first and second universal segments by preamplification is schematically illustrated in FIG. 10. Target-specific 3' ends of primers are shown as black arrows. "Primes" indicate complements: e.g., B'1, is complementary to B1. The 3' ends of amplicons can have a non-template 3' "+A-addition". As shown, first primer 1000 has a 3' portion that anneals to a first portion of first target nucleic acid 1002 and a 5' portion having a first universal segment (A1). Second primer 1004 has a 3' portion that anneals to a second portion of first target nucleic acid 1002 and a 5' portion having a second universal segment (B1-C1). PCR amplification yields amplicon 1006, which can be detected using any of the example universal detection formats described above, e.g., the universal detection format provided in FIG. 1. In FIG. 1, for example, each detection well has at least two primers. The 3' ends of these primers are complementary to all or a portion of the 5' ends of the pre-amplification primers. Referring to FIG. 1, at least one primer has a 5' tail with a dye and a quencher that is identical to the middle universal part of the opposite pre-amplification primer ($B_i$ in FIG. 1).

Preamplification can consist of a multiplex PCR that uses a low concentration (e.g., 10-100 nM) of primers with target-specific 3' ends and universal 5' tails that "encode" each target to be detected. The number of targets in the multiplex can depend on the number of fluorescent colors to be detected in the read-out device during the universal detection step, e.g., if the read-out platform uses 96 wells and detects in four colors, a total of N=96*4=384 targets can be multiplexed in a pre-amplification well. To assure accurate doubling during pre-amplification PCR, a small number of pre-amplification cycles (C), e.g., C=2-20, can be run. A more typical range of cycles is 10-16. In a preferred aspect, relatively low pre-amplification primer concentrations are used, e.g., 10-100 nM (typically 30-60 nM) to minimize primer dimer formation. Longer anneal-extend times—typically 2-10 minutes—and high polymerase concentrations can be used to compensate for low primer concentrations.

Pre-amplification primers have 5' universal segments, represented in FIG. 10 as A1 and B1-C1 for target 1, and $A_N$, $B_N$ and $C_N$ for the last of N targets. At the end of pre-amplification all N targets have been amplified ~$2^C$ times, e.g., $2^{10}$=1,024 times and universal DNA segments are linked into a single molecule.

Though it is possible to run pre-amplification and universal detection PCR in a single closed-tube reaction, a more typical application is to run a separate multiplex pre-amplification followed by optional dilution and splitting the reaction into multiple detection wells. Performing two PCR amplifications in separate tubes (or wells, etc.) can be more cumbersome than traditional single-tube real-time PCR. In reality, however, pre-amplification has to be performed anyway when (a) the amount of input DNA/RNA is low, e.g., single or a few cells and/or (b) detection volume is small. Several commercial platforms, e.g., BIOTROVE™ from Life Technologies or IFCs from Fluidigm, perform thousands of nanoliter scale PCR reactions compared to microliter scale typical for 96-well or 384-well plates. These platforms typically require pre-amplification due to low reaction volume. The pre-amplification reaction is typically diluted 1 to 100× or more and split into N wells if a single color per target is used or a smaller number of wells if several colors are used for detection in each well.

Also provided by the present invention are ligase-based linking strategies. Ligation or ligase chain reaction ("LCR", see U.S. Pat. No. 5,494,810) can be used as a method to add universal segments to one or more target nucleic acids of interest. Multiplex ligation assays are a well established technique, e.g., SNPLEX™ from Applied Biosystems and GOLDENGATE™ assays from Illumina. One can ligate DNA ligators on both DNA and RNA templates using appropriate ligases. The ligation reaction can be temperature cycled using thermostable DNA ligases to achieve amplification for target molecules. For example, see U.S. Pat. No. 5,494,810. Ligation assays generally have high specificity for detection of SNPs and rare mutations because ligases do not ligate nicks between 3' hydroxyl groups and 5' phosphates of the two ligator oligos, if there is a mismatch between the 3' end of the ligator and the target nucleic acid. Similar to the PCR-based pre-amplification described above, the ligation reaction can be diluted prior to universal detection.

Figure 11:
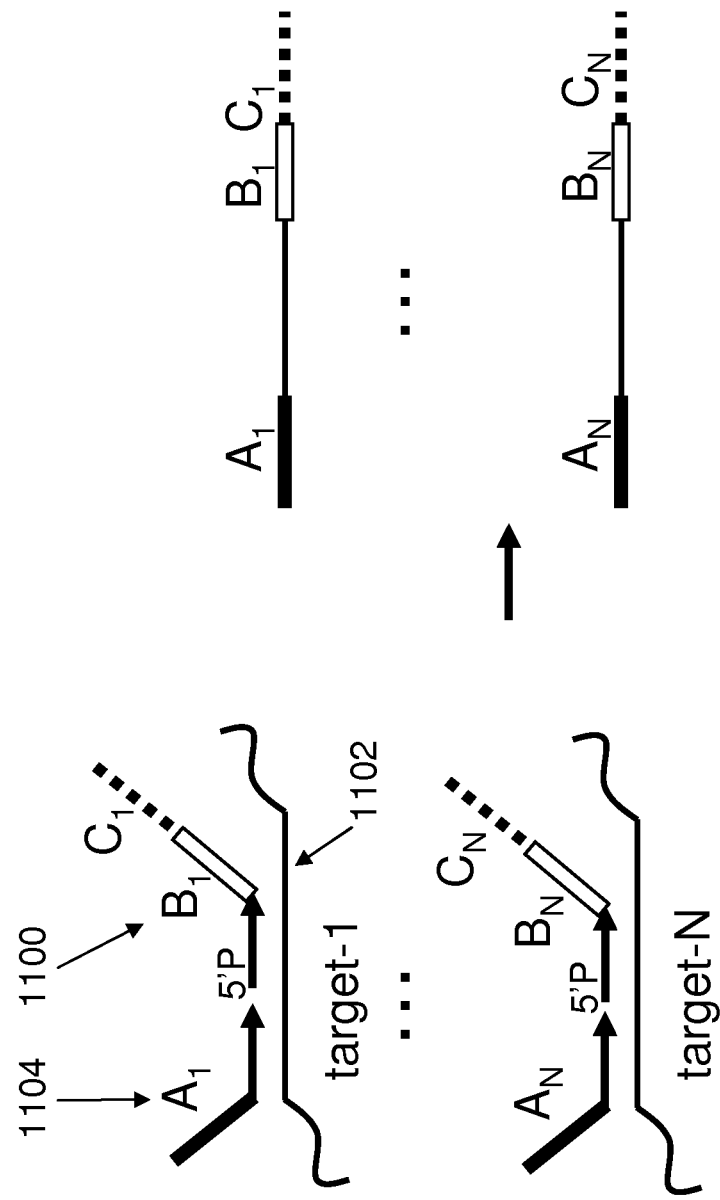
FIG. 11 schematically illustrates a ligation-based universal segment linking strategy.

An example ligase-based linking strategy is schematically illustrated in FIG. 11. As shown, first oligonucleotide 1100 has a 5' portion corresponding to first target nucleic acid 1102 and a 3' portion having the universal segment (e.g., universal segment $B_1$-$C_1$ in FIG. 11) phosphorylated 5' end and optionally blocked non-extendable 3' end. Second oligonucleotide 1104 has a 3' portion corresponding to first target nucleic acid 1102 and a 5' portion having the universal segment (e.g., universal segment $A_1$ in FIG. 11). Ligation of the 3' end of the second universal segment to the 5' phosphorylated end of the first universal segment links the two universal segments into a single molecule in a manner dependent on the first target nucleic acid. The resulting first tagged target nucleic acid can then be detected using any of the universal detection formats described herein.

Figure 12:
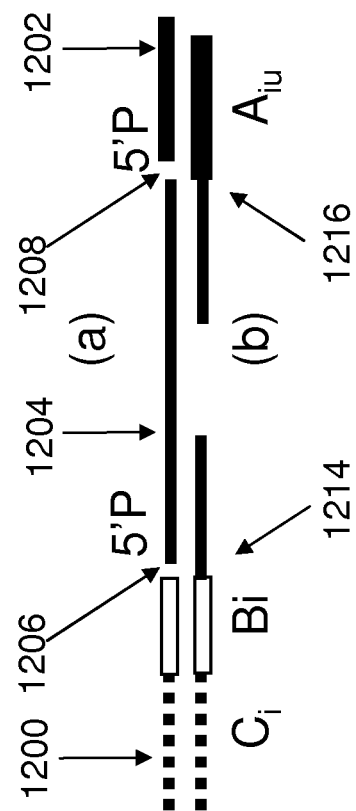
FIG. 12 provides a schematic illustration of a second ligation-based universal segment linking strategy.

FIG. 12 schematically illustrates a second ligase-based linking strategy. As shown, first universal segment 1200 and second universal segment 1202 are ligated to first target nucleic acid 1204 at ligation points 1206 and 1208, respectively. This method can be used when nucleic acids have defined ends, that occur either naturally or artificially, e.g., after using DNA restriction enzymes. The ligation depends on two complementary oligos 1214 and 1216 that span the nicks between the target nucleic acid and universal tags 1200 and 1202, providing the template for ligation.

It is preferable to remove unligated ligators from the reaction prior to universal detection. The unligated 5'-P ligator oligos (e.g., 1100 5'P-target-i-B1-C1-3' in FIG. 11) can be removed prior to PCR by, e.g., lambda-exonuclease treatment. This will prevent, e.g., the second universal primer (Ci) in FIG. 1 from priming on these ligators during universal detection. Alternatively, one can perform ligation on surface-bound target nucleic acid templates and wash off the unligated ligator oligos, e.g., as is done in the GOLD-ENGATE™ assay from Illumina.

Figure 13:
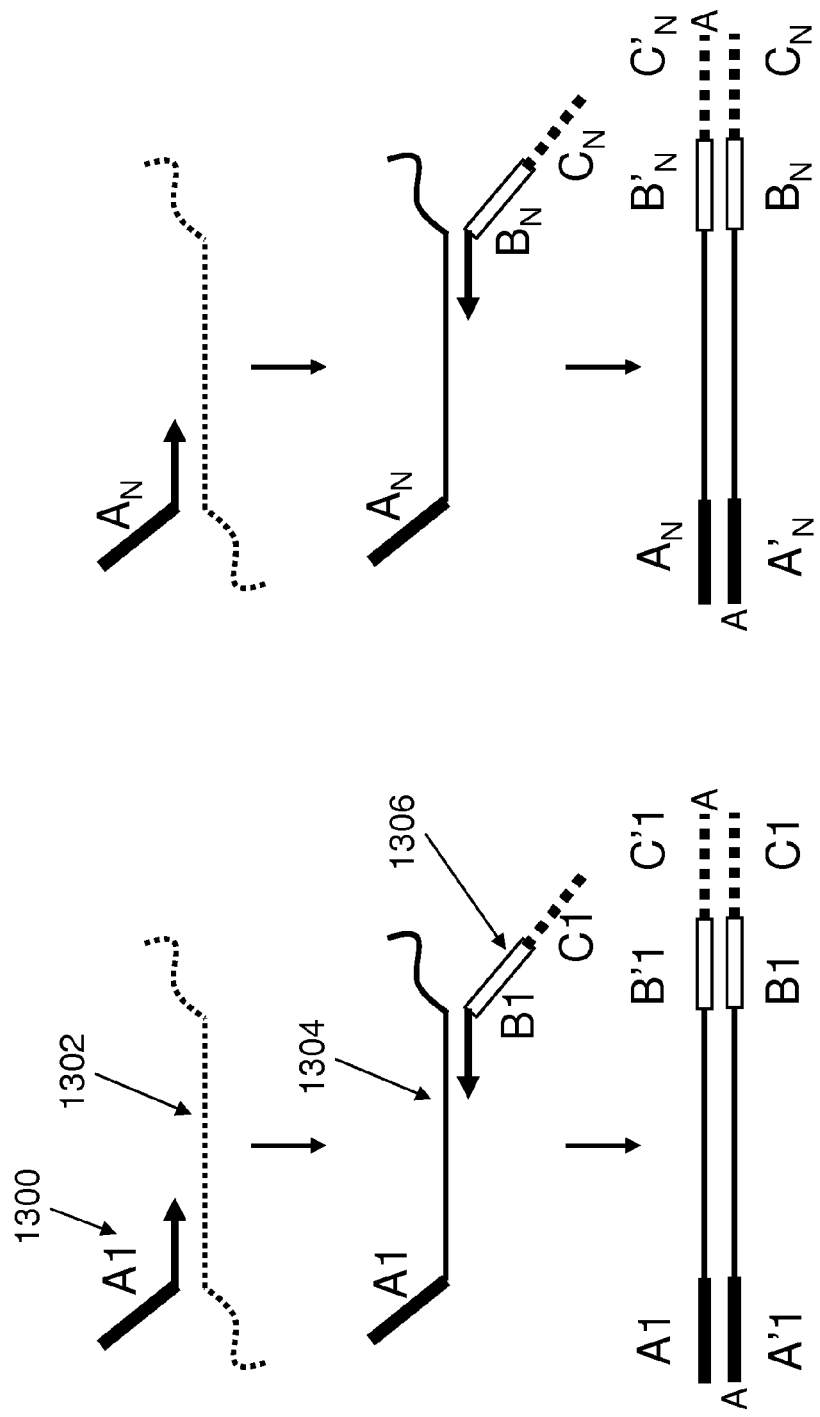
FIG. 13 schematically illustrates a strategy for linking universal segments into a single molecule based upon reverse transcription.

A further universal segment linking strategy, where the universal segments are linked into a single molecule by reverse transcription (RT), is schematically illustrated in FIG. 13. As shown, first primer 1300 has a 3' portion that anneals to first target RNA 1302 and 5' portion having a first universal segment (A1). Extension of the first primer yields first complementary DNA (cDNA) strand 1304. RT extensions using primers with target specific 3'-ends, especially when multiplexed, can generate non-specific extensions on the RT primers themselves. To minimize these non-specific extensions, the Ai tails (1300 in FIG. 13) are optionally blocked by complementary oligos that have blocked 3' ends or otherwise are non-extendable. Second primer 1306 has a 3' portion that anneals to first cDNA strand 1302 and a 5' portion having a second universal segment (B1-C1). Extension of the second primer yields double stranded cDNA product 1308, which can be detected using any of the universal detection formats described herein.

Figure 14:
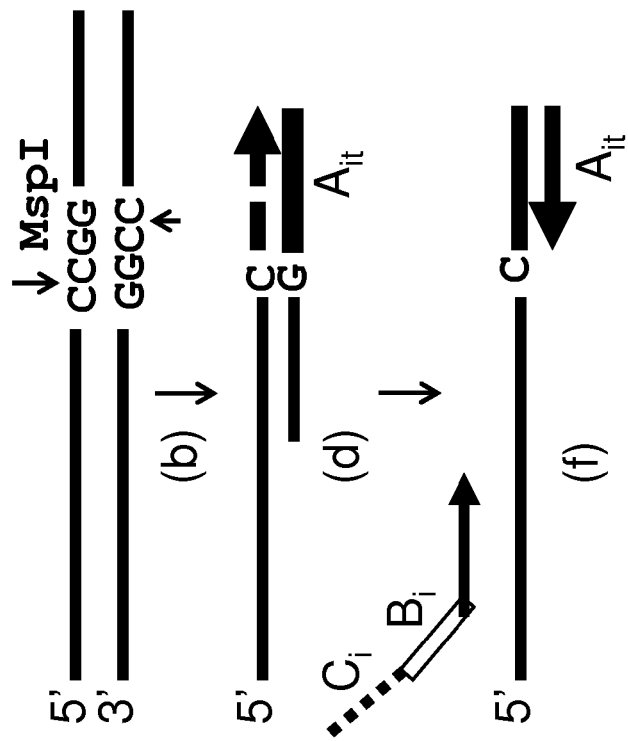
FIG. 14 provides a schematic illustration of a universal segment linking strategy based upon linear extension.
Figure 14:
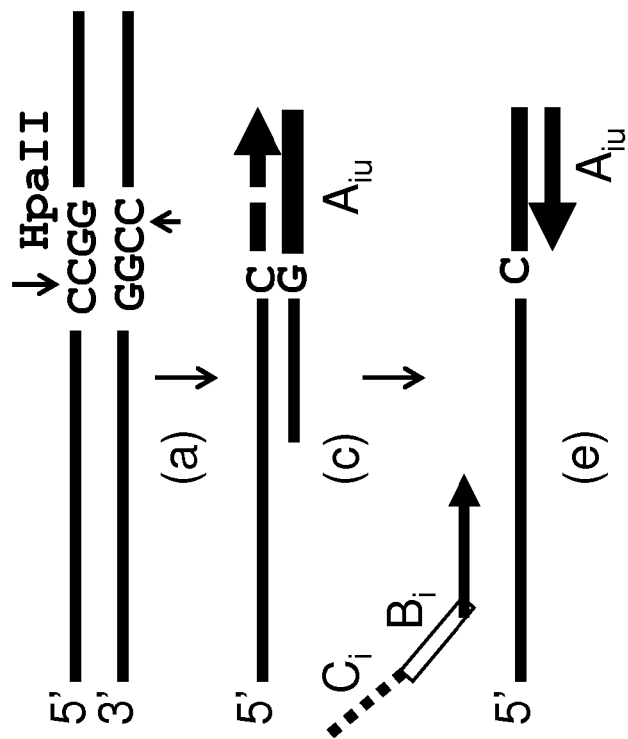

Linear polymerase extension can also be used to link the first and second universal segments together, so long as the target nucleic acid has a defined 3' end. An example linear extension linking strategy that can be used to detect methylation status is schematically illustrated in FIG. 14. As shown, the sample is divided into two and treated with (a) the methylation-sensitive restriction endonuclease HpaII (which cuts only unmethylated CCGG sites) and (b) the restriction endonuclease MspI, which cuts all CCGG sites regardless of methylation status. At (c) and (d), a pool of oligos is added to each sample to interrogate specific N CpG sites in the genome, with each oligo having tagged 5' ends (Aiu in (c), Ait in (d)), and target-specific 3' ends. A polymerase extends the 3' ends, replacing "CGG" with complements of the Aiu and Ait tagging sequences. The two sub-samples are optionally pooled together (e) plus (f), and multiplex PCR encoding is carried out with preamplification primers, e.g., similar to FIG. 15 below. As described elsewhere herein, universal detection measures methylation similar to the single nucleotide polymorphism detection described at FIG. 15, except real-time PCR is used and deltaCt values between the two colors in each well indicate the amount of methylated DNA in the sample. Typically, one needs to compare deltaCt values in a sample with 0% and 100% methylated control DNA samples to accurately measure methylation level in samples of interest.

Another methylation detection method provided by the present invention uses HpaII or any other methylation-sensitive enzyme or a combination of enzymes and places target-specific primer with encoding 5' universal segments on both sides of the target restriction sites. Generally, multiplex preamplification is performed for multiple methylation targets. This method, provided the restriction is complete, will measure only the amount of methylated DNA in the sample and will be able to detect small amounts of methylation in the sample, e.g., abnormally methylated cancer cells in the background of normal non-methylated DNA. One can multiplex encoding for methylation with CNV, somatic mutation, SNPs and other genomic DNA features of interest in a genomic DNA sample.

Exemplary Applications

The universal detection methods and compositions provided by the present invention are applicable for the detection of any type of target nucleic acid of interest. As noted above, exemplary target nucleic acids or nucleic acid features that can be tagged and detected in accordance with the present invention include DNA and/or RNA (e.g., from primates (e.g., humans), rodents, viruses, bacteria, Archaea, etc), cDNA, cDNA corresponding to a short RNA, a genetic variant, a mutation or insertion that confers drug resistance, a somatic mutation, a polymorphism, a single nucleotide polymorphism, a rare allele, a portion of the KRAS gene, a nucleic acid that exhibits a variation in copy number, an intron, an exon, an intron-exon boundary, a splice junction, one or more dinucleotides corresponding to one or more methylated or unmethylated CpG dinucleotides in bisulphite treated DNA, a nucleic acid comprising one or more restriction enzyme recognition sequences, a portion of human chromosome 21, a portion of the human X chromosome, and a portion of the human Y chromosome. It will be understood that any of the universal detection formats and universal linking strategies (and any combination thereof) can be used to detect these and other target nucleic acids and/or nucleic acid features of interest. The exemplary applications described herein are merely illustrative and do not serve to limit the types of target nucleic acids for which the present invention finds use.

Universal Detection of Polymorphisms and Somatic Mutations

Polymorphism detection is widely used in applications spanning clinical diagnostics, human disease research, epidemiology, sub-species identification and tracking, plant and animal breeding, quantitative trait loci (QTL) mapping, bacterial/viral strain typing, etc. Polymorphisms can be single nucleotide polymorphisms (SNPs), indels, multiple nucleotide polymorphisms (MNPs), inversions, etc.

Figure 15:
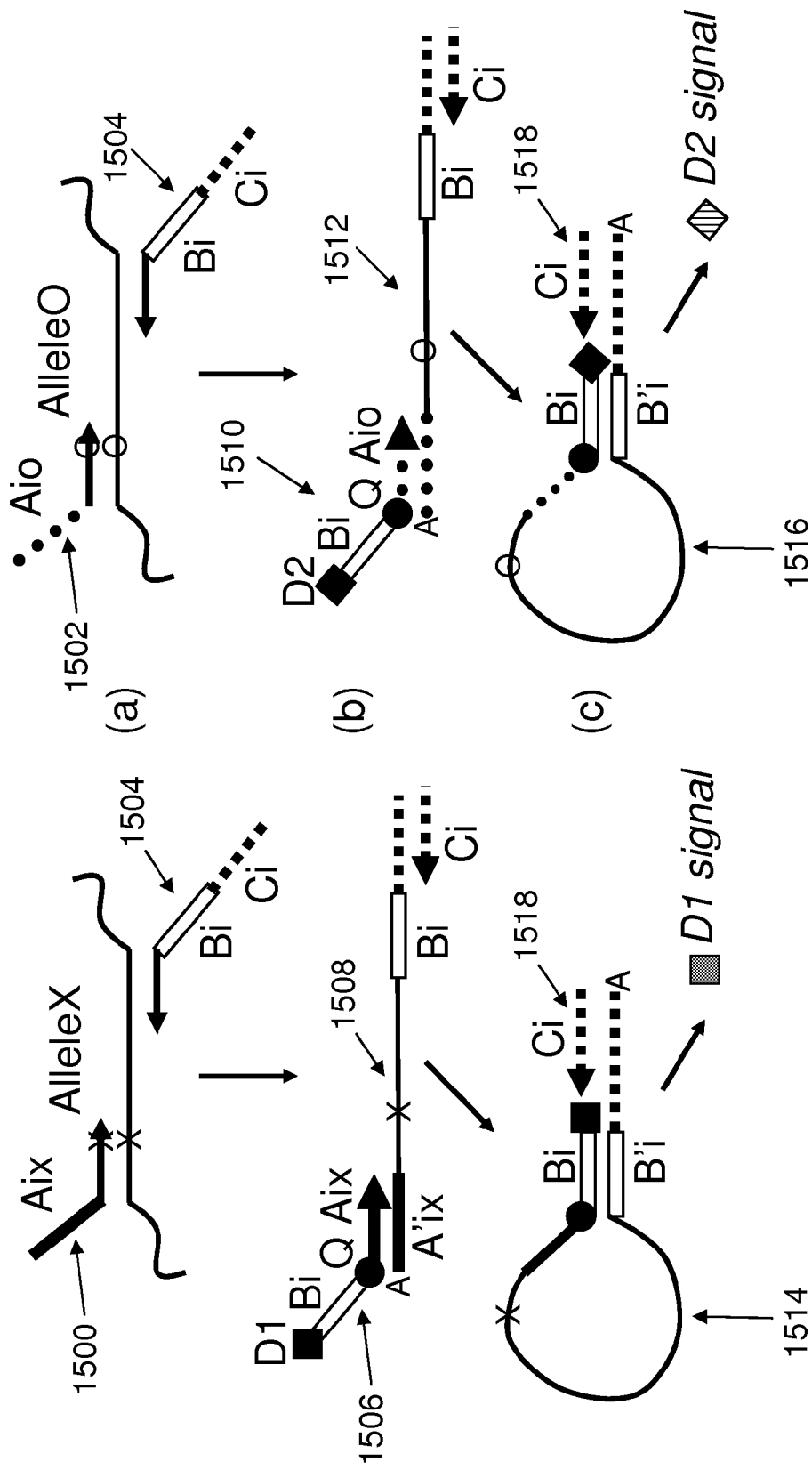
FIG. 15 schematically illustrates an example universal detection application for detecting nucleotide polymorphisms.

As an example of how methods and compositions of the present invention can be used to detect polymorphisms, a strategy for detecting SNPs is schematically illustrated in FIG. 15. At step (a), three primers per SNP ("i", where "i"=1 to N) are used for preamplification. First allele-specific primer 1500 has a 3' end specific for allele "x" of SNP "i", and second allele-specific primer 1502 has a 3' end specific for allele "o" of SNP "i". The 5' portions of the first and second allele-specific primers include universal segments, where the universal segments of the allele-specific primers are different. In FIG. 15, the 5' portion of first allele-specific primer 1500 has universal segment designated Aix, and the 5' portion of second allele-specific primer 1502 has universal segment designated Aio. Third common opposite strand primer 1504 has a locus-specific 3' end and a 5' portion having a universal segment (in this example, 5'-Ci-Bi). The pre-amplification PCR multiplexes 3*N primers in low concentrations to amplify N SNP loci. Assuming two color detection, the pre-amplification products are optionally diluted, e.g., 4-64 fold dilution, and split into N universal detection reactions.

In this example, universal detection is carried out using a format similar to that shown in FIG. 1. For SNP "i", PCR is performed using two differentially labeled primers. Here, D1 and D2 represent fluorescent dyes that can be distinguished from each other, e.g., by having different emission spectra. As shown at (b), first universal primer 1506 includes D1-Bi-Aix-3' and anneals at portion A'ix of amplicon 1508. Second universal primer 1510 includes D2-Bi-Aio-3' and anneals at portion A'io of amplicon 1512. Extension of the first and second universal primers generates extension products 1514 and 1516, respectively. The extension products form intramolecular hairpins having stems between Bi and B'i. Third universal primer 1518 (including portion Ci) anneals to portion C'i of extension products 1514 and 1516. 5' nuclease of a polymerase extending from the third universal primer removes the label D1 and D2 from extension products 1514 and 1516, respectively, generating fluorescent signal corresponding to allele "x" or "o" of the SNP "i" in colors D1 and D2, respectively.

Genotyping read-out can be done as an end-point to detect homozygosity and heterozygosity, or in real-time to accurately measure the ratio of the two alleles, e.g., for allele-specific expression or SNPs in copy number variation (CNV) regions. Polymorphism detection can be multiplexed, e.g., for two or three SNPs in each universal PCR well, provided the systems used are configured to detect and separate four or six fluorescent colors, respectively.

Somatic mutations occur, e.g., in cancer, and are often present in a very small portion of the sample DNA. Detection of specific mutations in the KRAS gene is used to select cancer therapeutics. For example, cetuximab does not work in tumors with certain KRAS mutations. In this case, only one "allele-specific" (for the mutation allele) primer can be used (as opposed to two for SNP genotyping), and several mutations can be multiplexed together based on same or different detection color. It is important to increase the specificity of allele-specific priming so that "wild type" predominant alleles from normal cells do not generate false positive signal. This application is often referred to as "rare allele detection". There are several ways to increase the specificity of priming for both SNPs and rare allele detection: (a) lower pre-amplification primer concentrations; (b) shorten the allele-specific 3' ends of the pre-amplification primers, and run the first cycles of pre-amplification at a lower temperature to engage short primers followed by regular cycling when the long tailed primers are engaged; (c) incorporate mismatches in the allele-specific primers close to the 3' end, where the presence of two mismatches has a synergistic effect on primer specificity; and incorporate modified bases close to the 3' ends of primers, e.g., as described in U.S. Pat. No. 6,794,142.

Universal Detection for Gene Expression

Figure 16:
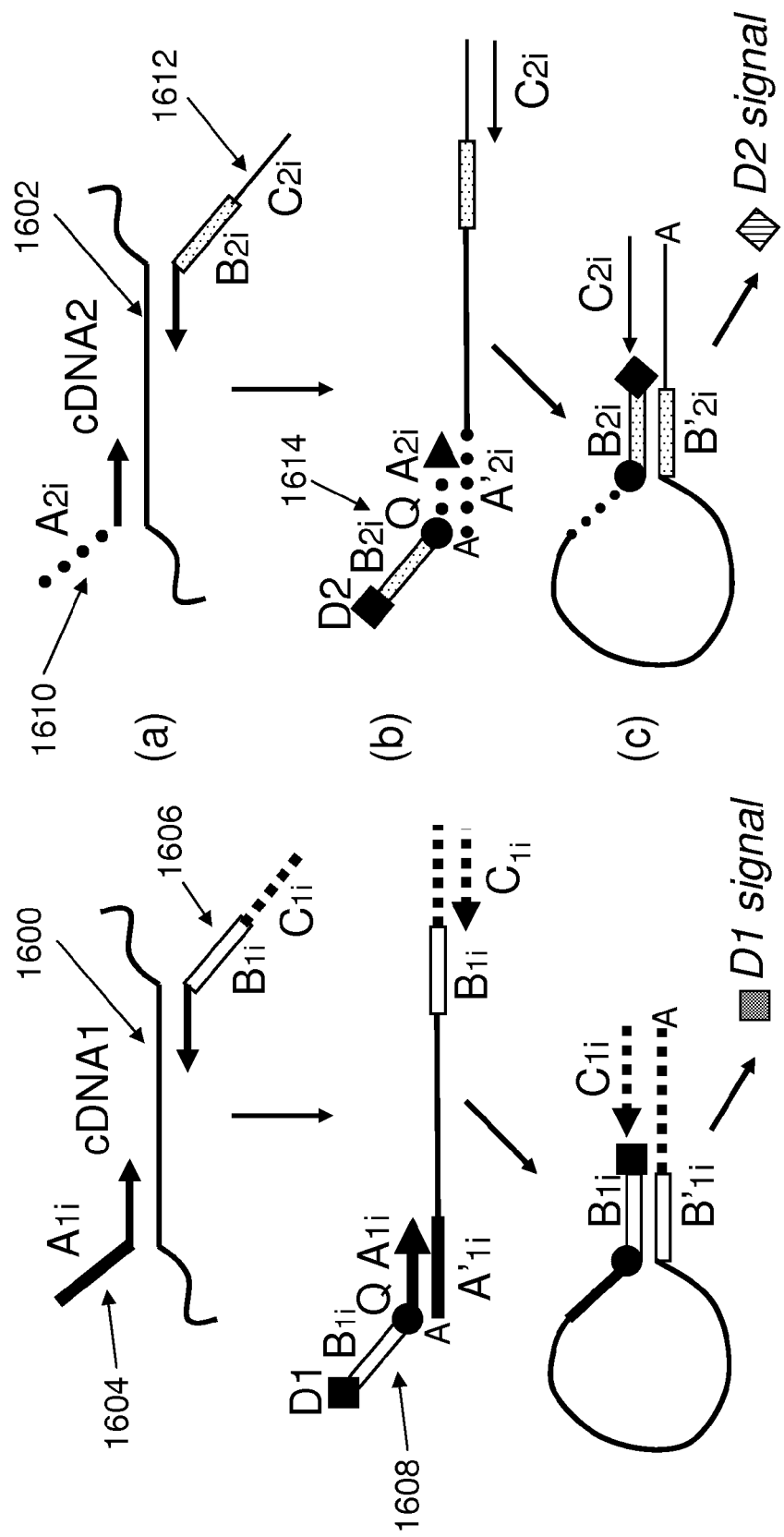
FIG. 16 provides a schematic illustration of an example universal detection application for detecting gene expression.

One of skill will appreciate that the universal detection methods and compositions of the present invention provide a powerful approach for measuring gene expression levels, including the simultaneous measurement of the expression levels of many different genes of interest. An exemplary strategy for simultaneously (e.g., in the same well) measuring the expression levels of two different genes is schematically illustrated in FIG. 16. Preamplification ("encoding") of cDNA 1600 corresponding to mRNA transcribed from a first gene and cDNA 1602 corresponding to mRNA transcribed from a second gene occurs at step (a). With respect to cDNA 1600 corresponding to mRNA transcribed from a first gene of interest, primer 1604 has a 3' portion that anneals to cDNA 1600 and a 5' portion having first universal segment 5'-A1i. Primer 1606 has a 3' portion that anneals to cDNA 1600 and a 5' portion having second universal segment A1i. Extension of first universal primer 1608 occurs at step (b), where first universal primer 1608 has a 3' portion (A1i) that anneals to portion A'1i of the amplicon generated during preamplification, and where first universal primer 1608 has a 5' portion that includes 5'-D1-B1i-Q. D1 is a first detectable label (e.g., a fluorescent dye) and Q is a quencher. At step (c), the product extended from first universal primer 1608 forms an intramolecular hairpin having a stem between portions B1i and B'1i. Subsequent to hairpin formation, second universal primer C1i anneals to the extension product and is extended by a polymerase. The 5' nuclease activity of the polymerase removes the first detectable label D1, such that D1 is no longer quenched by Q and emits a first detectable signal (e.g., a color that correlates to the presence or amount of cDNA 1600 in the sample).

Preamplification of cDNA 1602 occurs in a manner similar to that of cDNA 1601, but cDNA 1602 is "encoded" during preamplification with universal segments that are different than those used to encode cDNA 1600. Primer 1610 has a 3' portion that anneals to cDNA 1602 and a 5' portion having third universal segment 5'-A2i. Primer 1612 has a 3' portion that anneals to cDNA 1602 and a 5' portion having fourth universal segment 5'-C2i-B2i. Extension of third universal primer 1614 occurs at step (b), where third universal primer 1614 has a 3' portion (A2i) that anneals to portion A'2i of the amplicon generated during preamplification, and where third universal primer 1614 has a 5' portion that includes 5'-D2-B2i-Q. D2 is a second detectable label (e.g., a fluorescent dye) having an emission spectrum distinguishable from D1, and Q is a quencher. At step (c), the product extended from third universal primer 1614 forms an intramolecular hairpin having a stem between portions B2i and B'2i. Subsequent to hairpin formation, fourth universal primer C2i anneals to the extension product and is extended by a polymerase. The 5' nuclease activity of the polymerase removes the second detectable label D2, such that D2 is no longer quenched by Q and emits a second detectable signal (e.g., a color that correlates to the presence or amount of cDNA 1602 in the sample) that is distinguishable from the first detectable signal.

Real-time PCR is frequently used to measure gene expression. The methods and compositions provided herein can be used to measure expression for several splice junctions in a well, each using a different color. In gene expression applications (e.g., FIG. 16), each target can have two different pre-amplification primers (vs. one common primer for polymorphisms, methylation, etc.): 5'-A1 i-target1-3', 5'-C1i-B1i-target1-3' and 5'-A2i-target2-3', 5'-C2i-B2i-target2-3' (FIG. 16(a), assuming 2-color detection). The dye-labeled primers have a different 5' tails, e.g., D1-B1i-Q-A1i-3' and D2-B2i-Q-A2i-3' and generally two digesting primers can be used: C1i and C2i (FIG. 16(b), i=1 to N).

The strategy set forth in FIG. 16 is merely exemplary, and it will be understood that any of the universal detection formats and universal segment linking strategies described herein can be employed in accordance with the present invention to detect or measure the expression of one or more genes or any other DNA targets (simultaneously or otherwise).

Simultaneous Copy Number Variation and Gene Expression Measurement

Differential gene expression is typically due to transcriptional regulation, but it is becoming increasingly clear that copy number variations (CNVs) are frequent in humans and contribute to the differential expression level of genes that are located in chromosomal regions that exhibit variations in copy number. The universal detection methods and compositions of the present invention are well-suited to measure CNVs, much in the same way that gene expression is measured, but where the target nucleic acid of interest is a portion of a gene (e.g., an intronic region, a region spanning an intron-exon boundary, etc.), rather than a cDNA corresponding to an mRNA transcribed from a gene.

Figure 17:
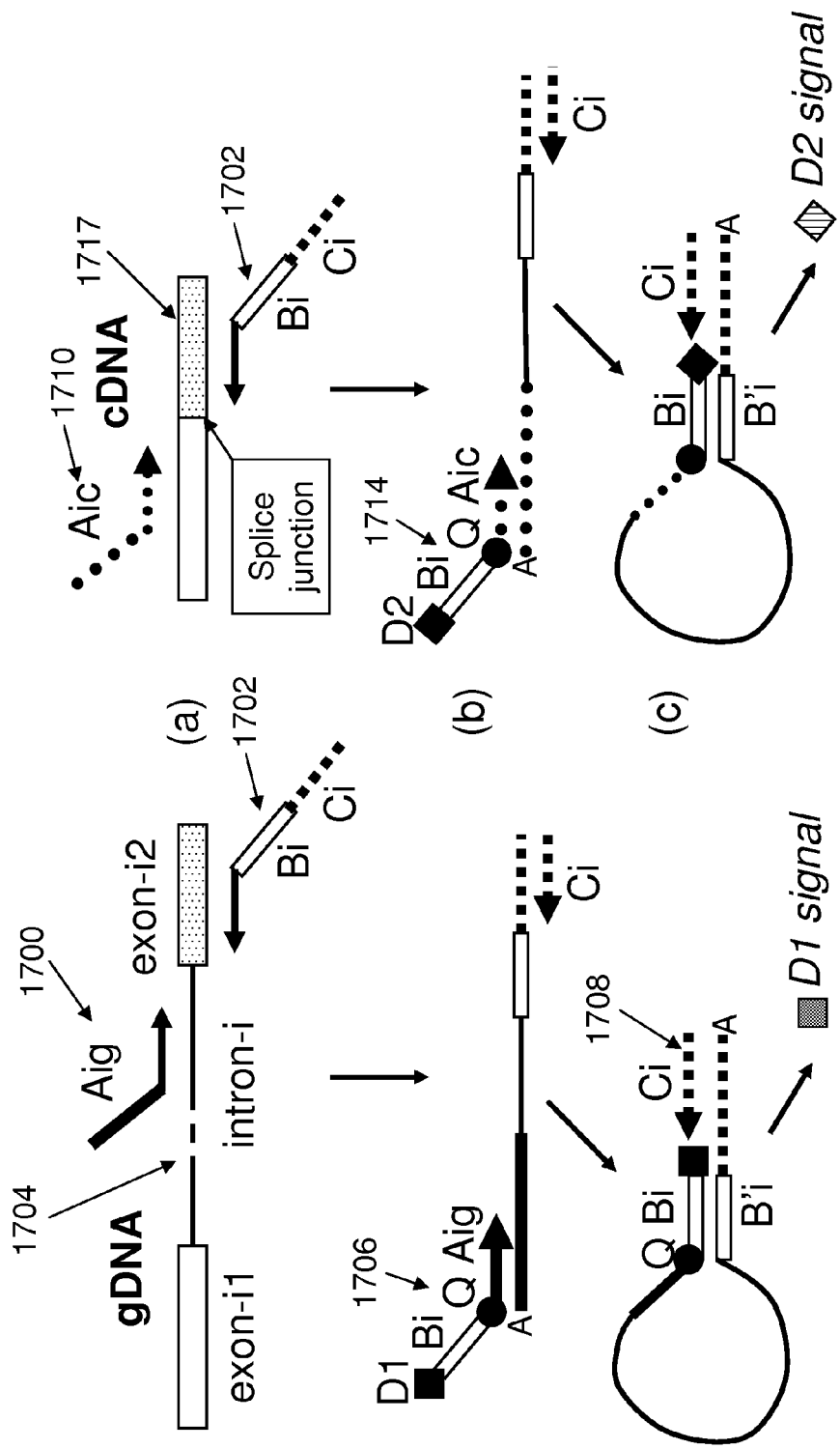
FIG. 17 schematically illustrates an example universal detection application for simultaneously determining copy number variation and gene expression.

Copy number variation can be measured alone, or can be measured simultaneously with the detection of other target nucleic acids that provide additional useful information, e.g., gene expression levels, methylation status, chromosomal abnormalities, and the like. An example application for the simultaneous measurement of copy number variation and gene expression is schematically illustrated in FIG. 17. To measure the number of copies of a target gene of interest in a sample (relative to a control sample), a preamplification reaction using first preamplification primer 1700 and second preamplification primer 1702 is performed at step (a). First preamplification primer 1700 has a 3' portion that anneals to an intron of gene 1704, and a 5' portion having first universal segment 5'-Ai. Second preamplification primer 1702 has a 3' portion that anneals to an exon of gene 1704, and a 5' portion having second universal segment 5'-Ci-Bi. At step (b), a 3' portion of first universal primer 1706 anneals to the amplicon generated during preamplification. First universal primer 1706 has a 5' portion that includes 5'-D1-Bi-Q, where D1 is a first detectable label (e.g., a fluorescent dye) and Q is a label quencher. First universal primer 1706 is subsequently extended by a polymerase, and at step (c), the extension product forms an intramolecular hairpin having a stem between segments Bi and B'i. Following hairpin formation, second universal primer 1708 (including segment Ci), anneals to the extension product and is extended by a polymerase. The 5' nuclease activity of the polymerase removes the first detectable label from the extension product, resulting in a first detectable signal from D1.

Simultaneous measurement of gene expression is shown at the right of FIG. 17. cDNA 1712 corresponding to an mRNA transcribed from gene 1704 is amplified using third preamplification primer 1710 and second preamplification primer 1702. Detection is initiated at step (b) by extension of third universal primer 1714 having a 3' portion that anneals to the preamplification amplicon and a 5' portion that includes 5'-D2-Bi-Q, where D2 is a second detectable label (distinguishable from D1) and Q is a label quencher. Third universal primer 1714 is subsequently extended by a polymerase, and at step (c), the extension product forms an intramolecular hairpin having a stem between segments Bi and B'i. Following hairpin formation, second universal primer 1708 anneals to the extension product and is extended by a polymerase. The 5' nuclease activity of the polymerase removes the second detectable label from the extension product, resulting in a second detectable signal from D2 that is distinguishable from the signal generated by D1. The amount of D1 signal (e.g., Ct-value for the first fluorescent color) correlates to gene copy number, while the presence or amount of D2 signal (e.g., a second fluorescent color) correlates to gene expression level. The second color D2 can be used to measure another genomic locus as a control. For example, the RNAse P gene locus always exists as two copies in a diploid genome, and can serve as a control that can be measured in the same well using color D2, while the target CNV is measured using color D1. In this case, CNV detection will be similar to cDNA detection as shown in FIG. 16, but using genomic DNA (gDNA) targets rather than cDNA targets. The deltaCt value between D1 and D2 in the same well corrects for pipetting errors and allows more accurate measurement of CNVs.

Two-Strand Universal Detection

The universal detection methods and compositions provided by the present invention can be used for two-strand detection of a target nucleic of interest. An exemplary approach for two-strand detection is schematically illustrated in FIG. 18. As shown, first tagged target nucleic acid 1800 includes first universal segment 1802 and second universal segment 1804. Both the first and second universal segments include two sub-segments: first universal segment 1802 includes Ai-Ei (and A'I-E'i), and second universal segment 1804 includes B'i-C'i (and Bi-Ci). First tagged target nucleic acid 1800 is denatured, and upon a subsequent decrease in temperature, first universal primer 1806 anneals to a first end of one strand of target nucleic acid 1800, and second universal primer 1808 anneals to a second end of the same strand of target nucleic acid 1800. First universal primer 1806 has a 3' portion that anneals to first universal segment 1802 and a 5' portion that includes 5'-D1-Bi-Q. Second universal primer 1808 has a 3' portion that anneals to second universal segment 1804 and a 5' portion that includes 5'-D2-Ei-Q. D1 and D2 are detectable labels that are distinguishable from each other, and Q is a label quencher. The first and second universal primers are extended to generate the extension products shown at (c) and (e), respectively. At (c), the extension product from first universal primer 1806 forms an intramolecular hairpin having a stem between Bi and B'i. Subsequent annealing and extension of second universal primer 1808 removes label D1 from the extension product, resulting in a detectable signal from D1. At (e), the extension product from second universal primer 1808 forms an intramolecular hairpin having a stem between Ei and E'i. Subsequent annealing and extension of first universal primer 1806 removes label D2 from the extension product, resulting in a detectable signal from D2 that is distinguishable from the signal generated by D1.

Universal Detection of Methylation Status

The present invention also finds use in detecting epigenetic features, e.g., features affecting the structure of genomic DNA which are not directly related to the primary DNA sequence. Methylation of genomic DNA and histones are common epigenetic features that affect genomic DNA structure and transcriptional regulation. Methylation of CpG dinucleotides in genomic DNA (met-C) is known to correlate with transcriptional regulation. For example, cancer cells often have abnormally methylated regions in the vicinity of transcription start points for tumor suppressor genes, causing down regulation of their transcription. Bisulphite converted DNA is frequently used to measure methylation levels in genomic DNA. Bisulphite treatment converts all unmethylated cytosines (C) into uracil (U) residues that behave as thymidines (T) during PCR. Bisulphite treatment does not convert methylated cytosines to uracils. As such, methylation detection according to the present invention can be performed in a manner similar to that described for SNP genotyping: if a given locus is detected as "CG", then that cytosine in the genomic DNA was methylated; if the locus is detected as "UG", then the cytosine was not methylated.

Figure 19:
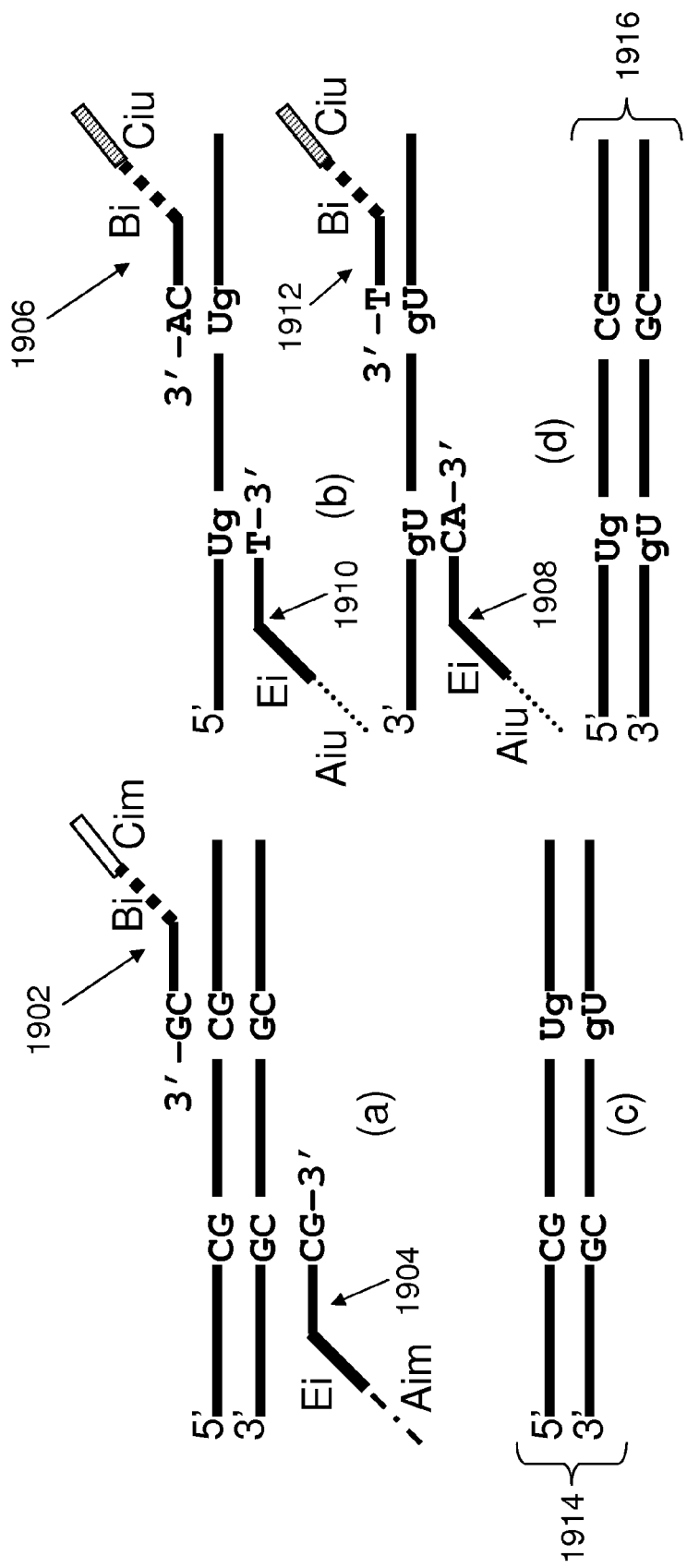
FIG. 19 provides a schematic illustration of an example encoding step for universal detection of methylation status of two CpG dinucleotides in bisulphite treated DNA.

An example approach for detecting the methylation status of a genomic locus of interest using the universal methods and compositions of the present invention, is schematically illustrated in FIG. 19. In this example, the methylation status of two closely-spaced CpG dinucleotides is performed using two-strand detection in two/four colors. Both strands are shown as they exist after bisulphite conversion; dsDNA is shown, although the sequences will actually be single-stranded. Pre-amplification encoding at (a) uses two met-C specific primers 1902 and 1904, but four primers for sites converted from C to U: two with a CA-3' end (1906 and 1908) that start at the first cycle and two with a T-3' end (1910 and 1912) that engage starting at the second cycle. Alternatively, one of the pairs, e.g., 1906 and 1910 can be used to detect one of the methylated strands. Molecules with only one methylated site are shown at (c) 1914 and (d) 1916. A total of N sites can be multiplexed during preamplification/encoding. The methylation status is encoded by the 5' tails: Aim and Cim for methylated DNA and Aiu and Ciu for unmethylated DNA. Two middle tags, Ei and Bi, encode two CpG sites. Four universal detection primers are used for the detection in four colors for each pair of methylation sites. the primers containing D1-Bi-Q-Aim-3' and D2-Ei-Cim-3' detect methylated DNA in colors D1 and D2 for the CpG sites shown at the left and right, respectively. The primers containing D3-Bi-Q-Aiu-3' and D4-Ei-Ciu-3' detect unmethylated DNA. The ratio of signals D1/D3 and D2/D4 correlate with percentage methylation for the left and right CpG, respectively.

Universal Detection for Measuring Short RNA Expression

Figure 20:
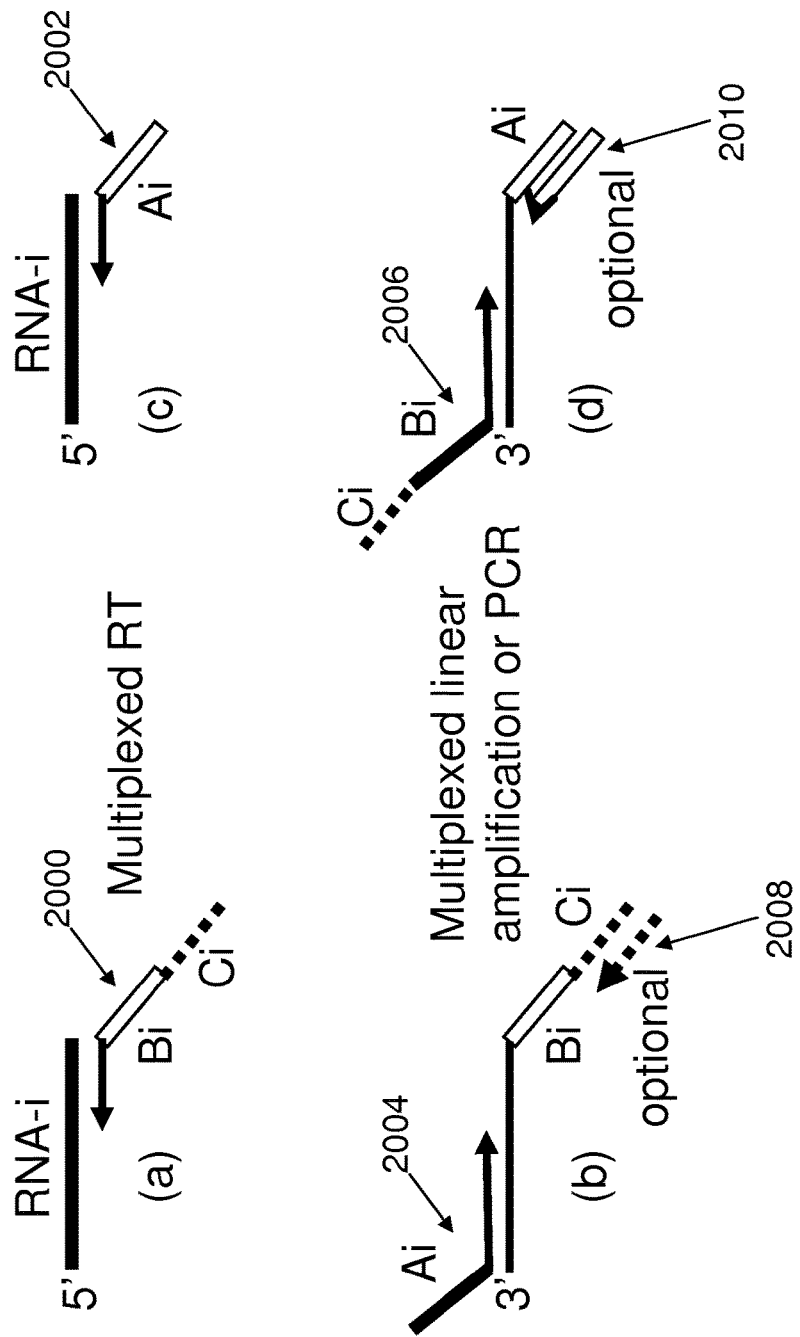
FIG. 20 schematically illustrates an example encoding step for universal detection of the presence or amount of one or more short RNAs in a sample.

Short RNAs present a challenge for TAQMAN™ detection as the length of the target RNA is not long enough for both primers and probes to anneal/hybridize. The universal methods and compositions of the present invention can be readily employed to detect such short RNA sequences. An example universal segment linking strategy ("encoding") method in accordance with the present invention for measuring expression levels of short RNAs, e.g., mature miRNAs, is schematically illustrated in FIG. 20. A reverse transcription (RT) step uses multiplexed RT primers (as shown, RT primer 2000 and RT primer 2002) with 3' ends matching the 3' ends of miRNAs and 5' universal segments tagging each miRNA sequence. These RT primers predominantly reverse transcribe mature miRNAs because the miRNA precursors are normally folded into stable hairpins. One can optionally add "blocking oligos" complementary to the universal 5' tails of the RT primers to minimize RT primers priming on other RT primers. The next step is linear pre-amplification (or alternatively, PCR) using forward primers (as shown, primer 2004 or primer 2006) with 5' universal segments and 3' ends specific to 5' ends of miRNAs (and optionally, primers 2008 or 2010 that match the 5' universal segment of the RT primers). Forward primers 2004 and 2006 may include one to three non-template Gs (guanosines) between the target-specific region and universal 5' tails, to stabilize forward primer annealing to the non-template Cs (cytosines) that RT often adds at the ends of RNA. Any of the universal detection formats described herein (e.g., the universal detection format illustrated in FIG. 1) can be used, with one or more colors per well based on how many miRNA species are multiplexed in a well.

Universal Detection of Drug Resistance Mutations

More accurate and powerful approaches for detecting mutations that confer drug resistance would greatly facilitate the individualized treatment of individuals affected by diseases, e.g., for which more than one treatment option is available. As will be appreciated, the universal detection methods and compositions provided by the present invention constitute a significant advancement in the field of personalized medicine.

The treatment of individuals infected with human immunodeficiency virus (HIV) typically includes a combination of three or more drugs. During the course of treatment, resistance to these drugs may develop, and it is advantageous to promptly replace the drug to which the HIV has developed resistance with another drug. The standard test used today involves Sanger sequencing of regions in the reverse transcriptase (RT) and protease inhibitor (PI) genes. This method is relatively expensive, takes a long time (10 days on average in a service lab) and can detect mutations only if they comprise >20% of total viral load. As provided by the present invention, known mutations that confer resistance to antiretroviral drugs administered in a drug cocktail can be encoded and detected in several hours in such a way that any resistance mutation to each drug is indicated by its own color, and a small percentage of mutated viruses in the viral population can be detected. Detailed and current information regarding mutations that confer resistance to antiretroviral drugs can be found at Stanford University's HIV Drug Resistance Database.

Figure 21:
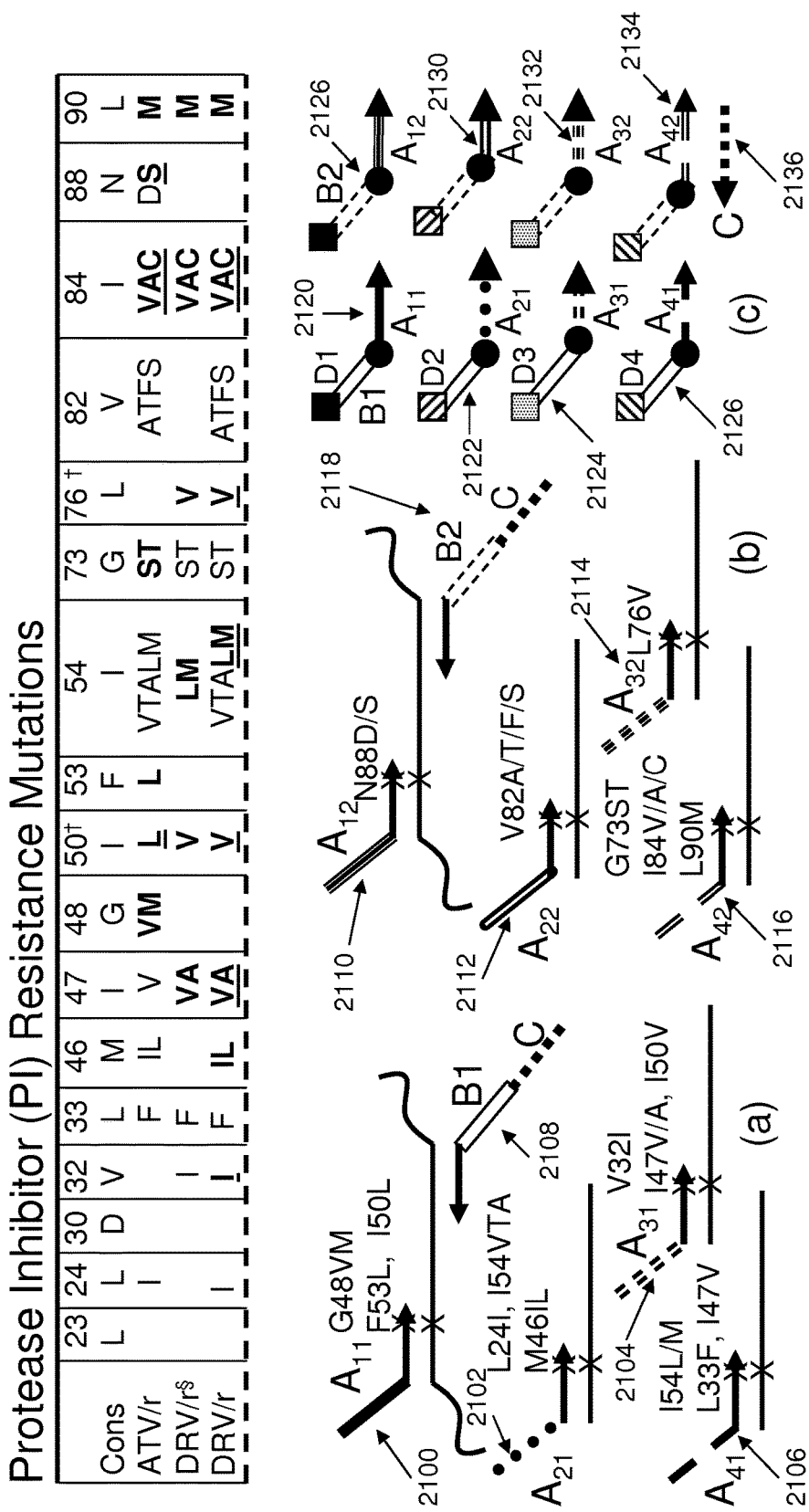
FIG. 21 schematically illustrates an example encoding step and universal detection of mutations that confer resistance to one or more HIV protease inhibitors.

An example of how the present invention can be used for multiplex mutation detection for HIV drug resistance is schematically illustrated in FIG. 21. Mutations in HIV protease that confer resistance to three protease inhibitors (ATV, DRV and FPV) are shown at the top of FIG. 21. Shown at (a) are mutation-encoding (preamplification) primers 2100-2106 for positions 24-54 and one locus-specific primer 2108 that includes C-B1-target-3'. For positions 73-90, shown at FIG. 21(b), mutation-encoding (preamplification) primers 2110-2116 and locus-specific primer 2118 that includes C-B2-target-3' are used. "X" designates the mutation-specific bases in viruses that are detected by complementary bases at the 3' ends of encoding primers; each mutation in general having its own primer with a mutation-specific 3' end. Shown in FIG. 21(c) are eight labeled universal detection primers 2120-2134 and universal primer 2136 (including segment C), which detect mutations such that drug resistance is indicated in one of the four colors: ATV resistance is indicated by D1; ATV and FPV resistance is indicated by D2; DVR and FPV resistance is indicated by D3; and resistance to all three drugs is indicated by D4. In addition, total viral load should be encoded by D5 and internal positive control (IPC) as D6 (not shown). FIG. 21 illustrates a general approach for encoding multiple targets (in this case different mutations that cause resistance to the same drug) to be detected in the same color. One can simplify this example by using same tags B1 and B2 and same $A_{j1}$ and $A_{j2}$ (j=1 to 4), so that four rather than eight labeled primers will be required for detection. One can also use the "switched format" detection method with a 5' quencher described above: when a color is detected during qPCR indicating that virus has developed a resistance, one can size fluorescent PCR products by capillary electrophoresis and determine which amino acid residue is mutated based on the length of the PCR product.

As an example, FIG. 21(a) shows encoding primer 2100 having A11-target-G48V-3' or A11-target-G48M-3' (top left corner) with a 3'-end that matches mutations that change the wild type 48G (glycine) to valine or methionine. These primers do not prime on the nucleic acid encoding the wild type 48G in HIV protease. This test will be simpler to use than the PCR Sanger sequencing test currently in use and will be able to detect less than 20% viral subpopulations that are not detectable by Sanger sequencing. For example, a GENEXPERT™ system from Cepheid can detect 6 colors in a cartridge, enabling the detection of resistance to three antiretroviral drugs as well as total viral load in a single cartridge in several hours. When mutated viruses are present, the test will indicate if resistance to each drug in a cocktail has emerged. Physicians can then modify the treatment cocktail/regimen accordingly.

The most frequently used HIV combination therapies (or "drug cocktails") have two nucleoside RT inhibitors (NRTI) and one non-nucleoside RT (NNRTI) or protease inhibitor (PI). Accordingly, four colors will be sufficient to detect four possible combinations of resistance to each drug and two NRTIs together. Detection colors are selected in such a way that each drug has a different detection color for all mutations that cause drug resistance. Several drugs used in a drug cocktail or candidates for treatment can be tested in multiplex using available colors in the detection instrument. One color can be used to measure total viral load.

High-Throughput Universal Detection

Exemplary Implementation on Integrated Fluidics Chips

Figure 22:
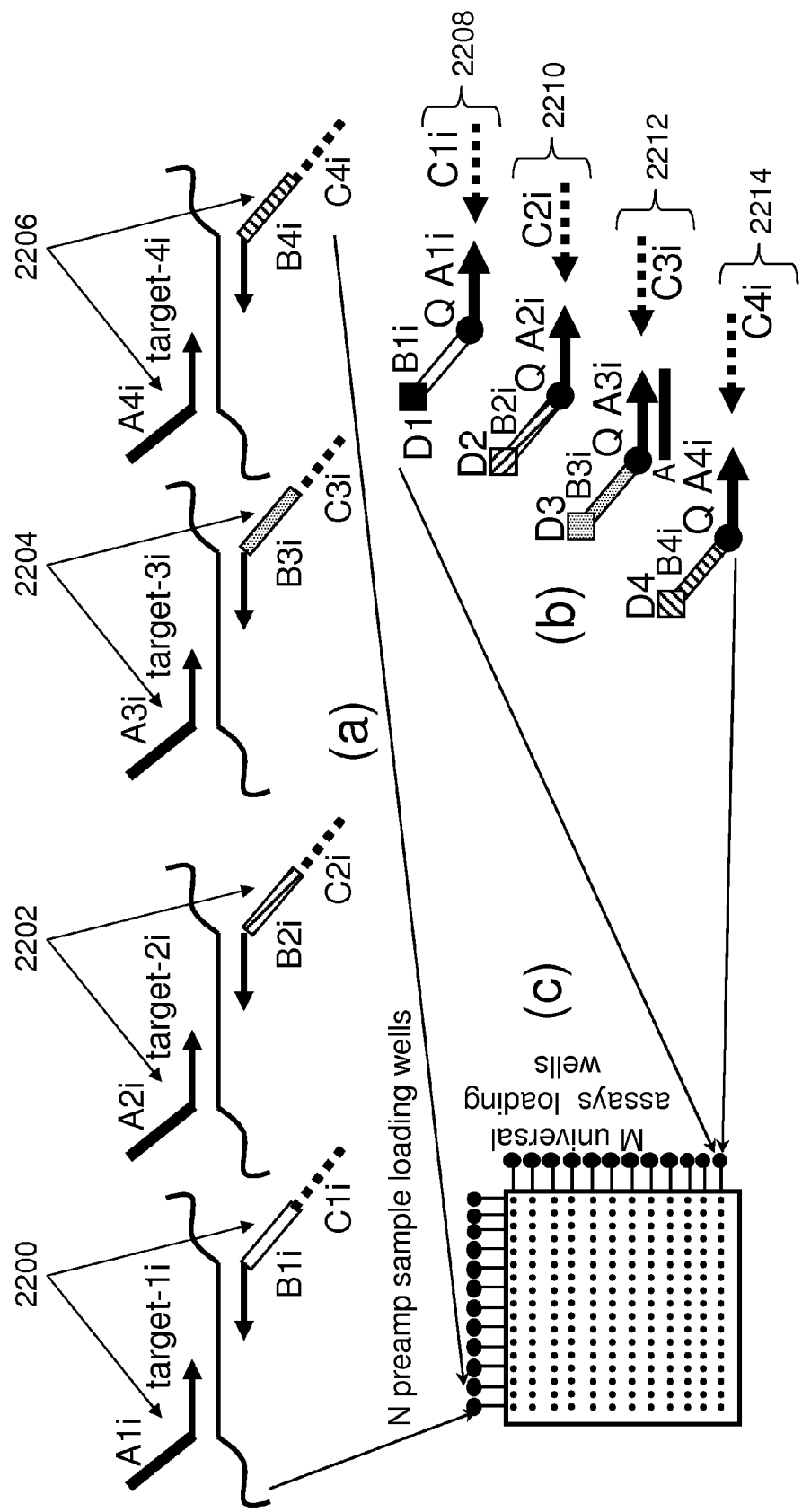
FIG. 22 provides a schematic illustration of an example multiplex encoding and detection in accordance with the present invention.

An example implementation of the universal detection methods and compositions of the present invention on integrated fluidics chips ("IFCs", e.g., those commercially available from Fluidigm) is schematically illustrated in FIG. 22. This example assumes four-color detection, although any number of colors detectable by the instrument can be used. The IFC has N sample and M assay loading wells so that the total number of detectable targets is 4*N*M. Currently available IFCs are N=M=48 (48×48) and N=M=96 (96×96). If the goal, for example, is to measure 8*M targets in a sample, two pre-amplification PCRs, each for 4*M targets each are performed for N/2 samples and PCR pre-amplification products for each sample are loaded into two sample-loading wells. Four preamplification primer sets 2200-2206 are shown at FIG. 22(a). A total of 4*M primers are used in each pre-amplification PCR. M universal detection primer sets 2208-2214, four primers each, FIG. 22(b) are loaded into M orthogonal loading wells ("i", where i=1 to M). Universal detection primer set 2208 detects nucleic acids tagged using preamplification primer set 2200, and so forth. N pre-amplification reactions are mixed with M universal detection assays and 4*N*M targets are measured using real-time (quantitative) PCR and/or end-point (e.g., "digital") PCR in N*M wells (FIG. 22(c)).

The 8*M targets used in this example (FIG. 22) can be any combination of SNPs, somatic mutations, CNVs, translocations, etc., all multiplexed together from the same gDNA sample. Gene expression, miRNA and/or methylation targets can also be included among the 8*M targets using separate sample preps and shared or additional pre-amplifications.

Digital PCR

Digital PCR is a method to accurately count the number of DNA molecules in a sample. For example, see U.S. Pat. No. 6,143,496. The method requires a small number of target DNA molecules and a large number of wells or droplets, the latter generally higher than the first. Assuming single-molecule PCR sensitivity and specificity, one can count the number of negative and positive wells/droplets and assuming random distribution to accurately count the initial number of target molecules in the sample. When using approaches provided by the present invention for digital PCR, the number of pre-amplification cycles and post-amplification dilution are adjusted such that the number of target molecules is smaller or similar to the number of digital PCR mini-wells or droplets. As provided by the present invention, digital PCR can be used to count any nucleic acid target, e.g., genomic DNA targets, methylated DNA, mRNA/miRNA/ncRNA, viruses, mutated viruses, etc.

Methods known in the art can be used to deliver universally tagged target nucleic acids (e.g., pre-amplified DNA) to multiple distinct digital count detection containers, e.g.: (1) traditional 96-384-1,536-3,072 and so on well micro-titer plates; (2) Fluidigm and BioTrove use thousands of mini-wells in specialized nano-fluidics devices; (3) systems from 454 Life Sciences/Roche use a PICOTITERPLATE™ device with more than a million wells; or (4) small droplets can be made by emulsion PCR (ePCR, currently used commercially by 454/Roche and SOLID™/Life technologies) or specialized devices to make small water droplets in oil, e.g., RainDance RAINSTORM™ or QUANTALIFE™. Digital counts of positive droplets (e.g., droplets positive for detectable signal generated by the detection steps of the universal detection methods of the present invention) and negative droplets can be counted using a counting device.

Figure 23:
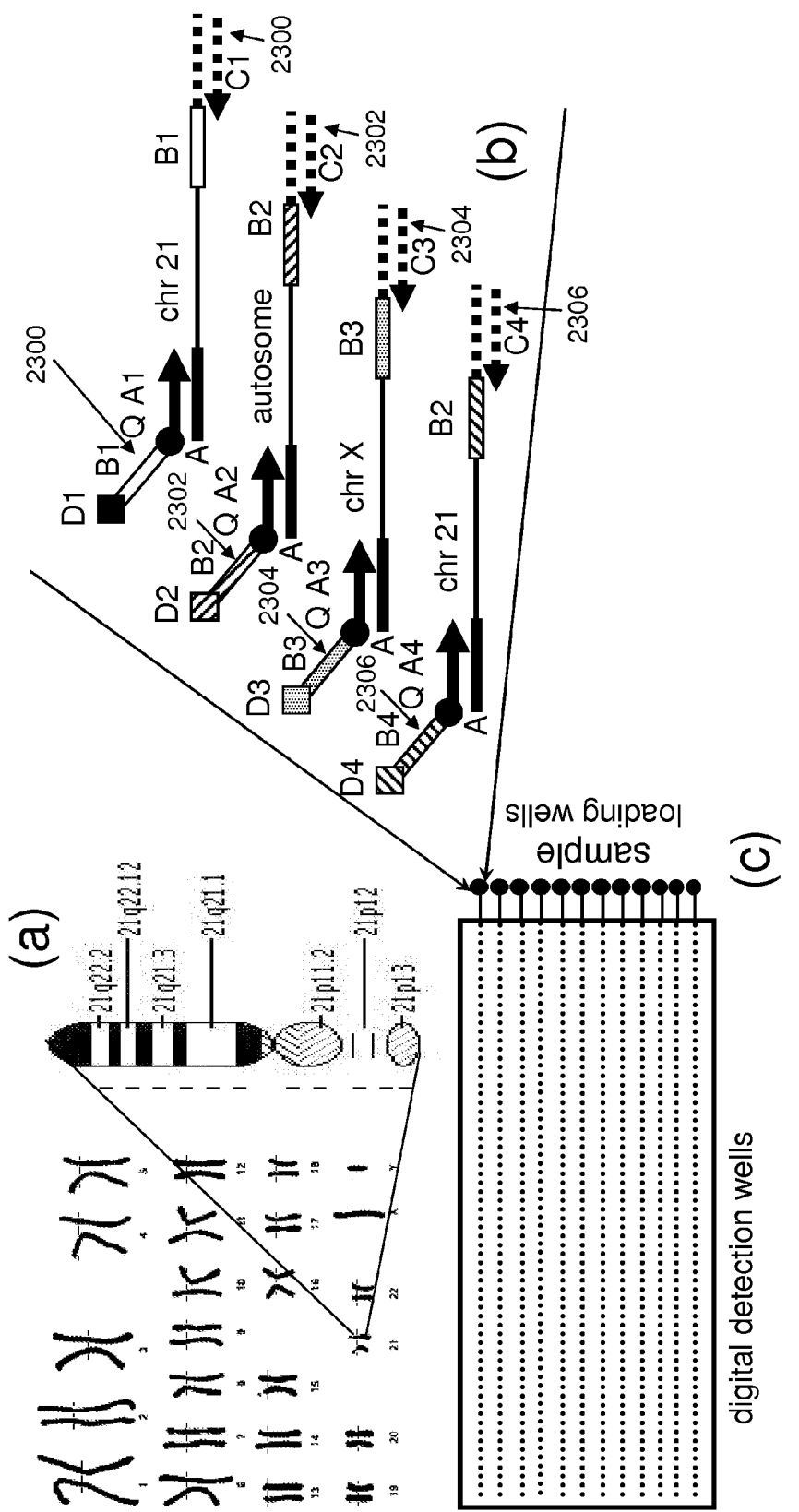
FIG. 23 schematically illustrates an example strategy for detecting trisomy 21 via digital PCR in accordance with the present invention using universal middle tags.

FIG. 23 schematically illustrates an example digital PCR method for diagnosing trisomy 21 (T21) in DNA from mother's blood using an integrated fluidics chip in accordance with the present invention. As shown at (a), 48+48 unique targets are selected from chromosome 21, 48 are selected from other autosomes, and 48 are selected from chromosome X for a total of 192 loci. A single 192-plex preamplification ("encoding") PCR is diluted, e.g., to approximately 400-1,000 molecules for each chromosome and mixed with four universal detection primer sets 2300-2306 (shown at FIG. 23(b)) that anneal to the universal segments corresponding to the Down syndrome critical region (DSCR) on chromosome 21 (2300), autosomes (2302), the X chromosome (2304) and remaining portions of chromosome 21 (2306). As shown at (c), each universal detection reaction is loaded onto one of 12 loading wells (large circles) and split into 1,000 mini-wells or droplets (small circles in dashed line) for universal detection using the methods and reaction mixtures of the present invention. 48,000 dPCR data points (12*1,000*4 colors) will permit an accurate calculation of the number of tagged target nucleic acid molecules for chromosome 21, autosomes and chromosome X, based upon the number of positive and negative wells or droplets in each color.

One can perform digital count for T21 detection using universal ePCR (FIG. 7). The beads for ePCR have four universal detection primers: Q-B1-D1-spacer-surface-spacer-A1-3', Q-B2-D2-spacer-surface-spacer-A2-3', Q-B3-D3-spacer-surface-spacer-A3-3' and Q-B4-D4-spacer-surface-spacer-A4-3' (e.g., FIG. 7(a) shows two such primers). The pre-amplification products and the universal "C" primer (e.g., see FIG. 7(b)) are used in the ePCR with the four-primer beads, so that each droplet has on average less than one pre-amplified target in each color. During ePCR several tens of thousands of 5' nuclease-specific fluorescent dye molecules will be unquenched on each bead as result of the exponential amplification starting from a single pre-amplified molecule (FIG. 7 (c)-(d)). Next, the ePCR emulsion is broken and the beads are deposited on the slide surface. The read-out has several steps: (1) the total number of beads is counted in white light; and (2) the fluorescent detection is performed in four colors, with each bead can be positive for as many as four colors. Given the importance of avoiding false negatives, two optional additional controls steps can be performed: one or several cycles of hybridization using a set of labeled in four color probes that are specific to each of the targets used for detection (this orthogonal direct target detection is used to confirm the sequence that gave rise to the universal detection signal on each bead; and treatment of the slide with reagents that cut the bond between the quencher from the dye, so that every bead shows signal in four colors. This can be done, e.g., if uridine, THF, or oxo-G is present between the quencher and the dye and the enzymatic treatment with UDG/EndoV/Fpg, respectively, is used to cleave off the quencher from all beads. The total unquenched signal effectively estimates the number of universal primers bound to each bead during manufacturing. This signal can be compared to the universal detection signal to better distinguish between real and false positive signal on each bead. Essentially, we normalize signal per bead given that during bead manufacturing, a different number of universal primer molecules can be attached to each bead.

The number of the pre-amplification molecules for chr21, autosomes and X can be compared. Given that each slide can have hundreds of millions of beads, a small 2.5% increase in chromosome 21 counts relative to other autosomal and X chromosome counts can be detected and used to diagnose trisomy 21. The same test will also detect X-chromosome aneuploidy, e.g., triple-X, XXY, and/or XO.

The universality of the detection primers of the present invention makes it much easier to develop detection on the beads or on the surfaces: the same beads or slide surfaces can be used to detect any set of targets. But in cases where a very large number of samples needs to be tested, e.g., for detection of trisomy 21, one can use target-specific labeled primers (e.g., as in FIGS. 7-9), on the beads or on the slide surfaces to directly measure nucleic acids or use non-tailed primers to pre-amplify genomic DNA/RNA.

Figure 24:
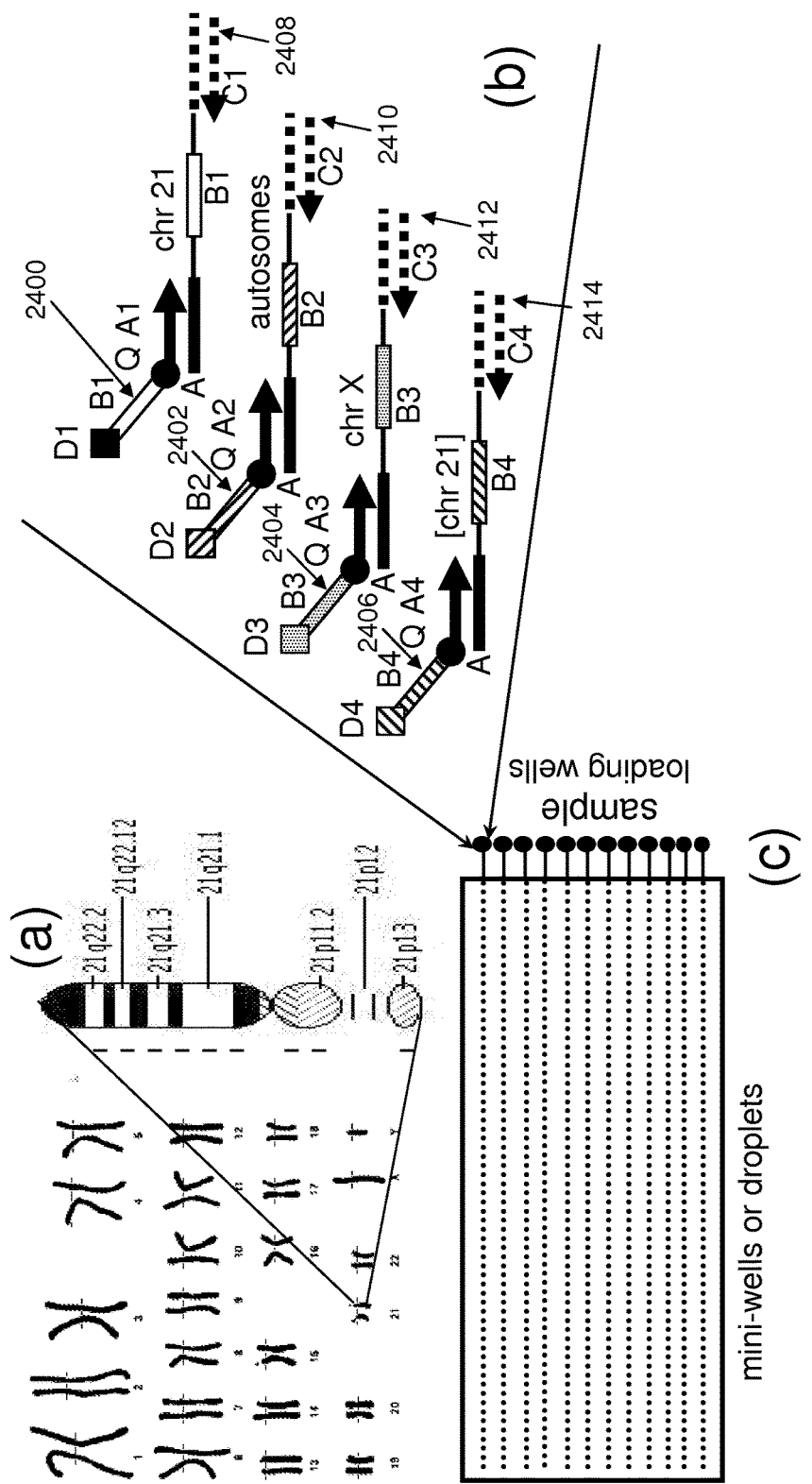
FIG. 24 provides a schematic illustration of a second strategy for detecting trisomy 21 via digital PCR in accordance with the present invention using naturally occurring short middle tag sequences.

A second approach provided by the present invention for diagnosing trisomy 21 via digital PCR is schematically illustrated in FIG. 24. First, one selects short B1 sequences that occur more than 48 times in the Down syndrome critical region (DSCR) on chromosome 21, another sequence B2—in autosomes, B3—in chromosome X and B4 in remaining portions of chromosome 21. 48 encoding primer pairs with 5' universal segments ("tails") A1/C1 are designed to amplify 48 B1 loci in DSCR. 96*3=288 encoding primer pairs with tails A2/C2, A3/C3 and A4/C4 are designed to amplify loci that with sequences B2, B3 and B4 in respective chromosomes. As shown at (b) universal primers to detect tagged target nucleic acids from DSCR have short 5'-tail B1 labeled in D1 (universal primer 2400), autosomal targets have tail B2/D2 (universal primer 2402), chromosome X targets have tail B3/D3 (universal primer 2404), and the rest of chromosome 21 having tail B4/D4 (universal primer 2406). A single 48+288=336-plex, or alternatively, 12×28-plex or any combination in-between of multiplex encoding PCR reactions are performed (not shown). Twelve preamplified ("encoded") samples are diluted to approximately 4,000-8,000 molecules for each target and mixed with the four labeled universal detection primers 2400-2406 and corresponding reverse universal detection primers 2408-2414 (b) that target DSCR, autosomes, the X chromosome and the rest of chromosome 21. As shown at (c), each universal detection reaction is loaded into one of 12 loading wells (large circles) and split into 10,000 mini-wells or droplets (small circles). 480,000 dPCR data points (12*10,000*4 colors) permit accurate calculation of the number encoded molecules for chromosome 21, autosomes and the X chromosome based upon the number of positive and negative wells or droplets. It will be understood that the present invention contemplates any number of sample loading wells, assay loading wells, and reaction locations (e.g., detection wells) For example, 1,000 or 10,000 wells or droplets, 12 loading wells, 48 or 96 targets for DSCR, X, autosomes, etc. can be used.

Other prenatal and clinical testing can include CNVs, translocations, etc. As personalized genomics and pharmacogenomics applications expand, SNP, CNV, gene expression, miRNA, methylation and rare allele detection via the methods and compositions provided by the present invention can be used for both clinical and research use.

One possible application is cancer diagnosis and/or cancer pharmacogenomics, but there are other clinical conditions where this approach can be used. For example, one can detect multiple viral and or bacterial pathogens in a sample. Cancer is linked to many underlying genomic, epigenomic and gene regulation changes. SNPs and other inherited (germ line) polymorphisms can predispose to cancer, e.g., BRCA1/2 gene alleles. In addition, somatic mutations, large genomic rearrangements, e.g., translocations (BCR-ABL is the most well-known), CNVs (including loss or heterozygocity) and other changes in genomic DNA are linked to cancer. It is well established that cancer and pre-cancerous cells have different gene and miRNA expression patterns as compared to normal cells. Patterns of differential gene expression are used to differentiate between different types of leukemias. For example, Genomic Health Inc. has commercialized the ONCOTYPEDX™ test to measure expression levels for 21 genes and recommend chemotherapy for breast cancer patients based on the results. Cancer has many different causes and a large number of available chemotherapeutic drugs either work or do not work depending on the underlying genetic abnormalities (somatic mutations, methylation, gene regulation, etc.).

Figure 25:
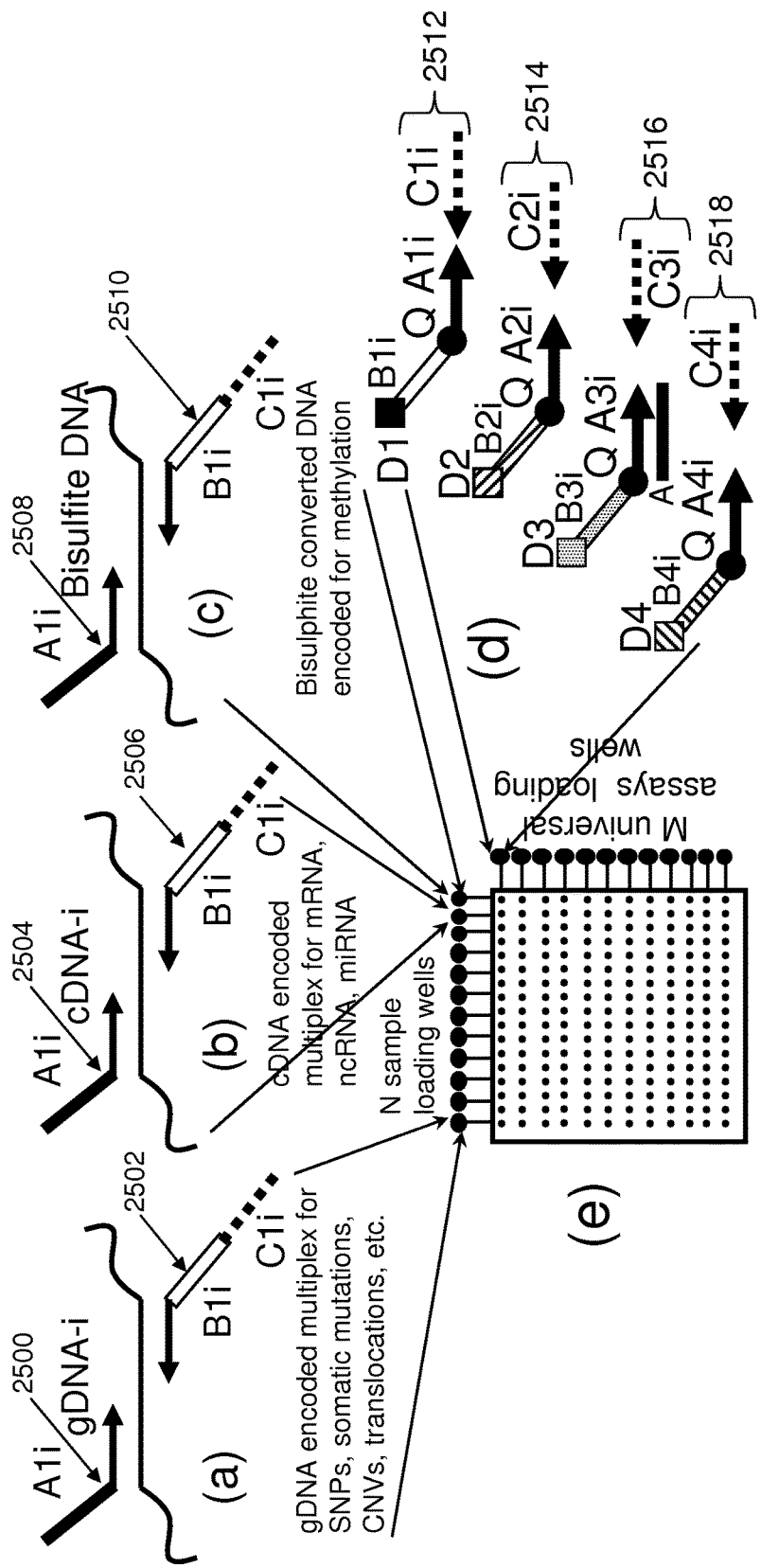
FIG. 25 schematically illustrates an example strategy for detecting a variety of target nucleic acids, the results from which can be combined into a diagnostic output or treatment outcome.

FIG. 25 schematically illustrates an example diagnostic application using the universal detection methods and compositions of the present invention. Here, an integrated fluidic chip (IFC, e.g., from Fluidigm) is used, and SNPs and/or somatic mutations (FIG. 25(a), mRNA/miRNA expression (FIG. 25(b)) and methylation (FIG. 25(c)) are encoded by preamplification PCR which links universal segments for each particular target. The target nucleic acid in each of the N sample-loading wells has to be encoded by 4*M encoding primers; only encoding primers that are decoded by $A_{1i}$, $B_{1i}$ and $C_{1i}$ in color D1 are shown. The encoding primers with tails 5'-$A_{2i}$/5'-$C_{2i}$-$B_{2i}$, 5'-$A_{3i}$/5'-$C_{3i}$-$B_{3i}$ and 5'-$A_{4i}$/5'-$C_{4i}$-$B_{4i}$ are not shown. As shown at FIG. 25(a), preamplification ("encoding") primers 2500 and 2502 have 3' portions specific to one or more genomic DNA targets, e.g., polymorphisms (e.g., SNPs), somatic mutations, CNVs, translocations, and the like. Preamplification primers 2504 and 2506 have 3' portions specific to a cDNA corresponding to an mRNA, an miRNA, an ncRNA, and the like. Preamplification primers 2508 and 2510 have 3' portions specific to a genomic DNA target containing one or more CpG sites for which the methylation status will be interrogated. The 5' portions of preamplification primers 2500-2510 include universal segments that encode the desired genomic target for subsequent detection using the corresponding universal detection primer pairs shown at FIG. 25(d).

The tagged target nucleic acids from the linking/encoding step at FIG. 25(a)-(c) are detected using the four universal primer pairs 2512-2518 shown at FIG. 25(d). Each of the four universal primer pairs are differentially labeled and have 3' portions specific to the corresponding universal segments linked to the nucleic acid targets at (a)-(c). The tagged ("encoded") target nucleic acids and the universal primers are delivered to reaction locations on the IFC (shown at FIG. 25(e)) where universal detection occurs. It will be understood that IFCs can be preloaded with the universal detection primers. For example, IFCs can be sold with the universal detection primers already present in assay loading wells or the reaction locations, and the end-user need only load the tagged target nucleic acids into the IFC before universal detection can be carried out in accordance with the present invention. The results for each sample can be combined together into a diagnostic output, e.g., a recommended treatment.

As shown in FIG. 25, methods and compositions of the present invention method can be employed to detect any combination of multiple genomic, RNA, methylation targets, and the like, on an IFC. Using four colors, a total of up to 36,864 targets and controls can be measured in a 96×96 IFC. A wide range of samples can be used, e.g., 96 cells from the same individual, several tumor and normal tissue control samples for a few patient or 96 different patient samples. The data from all targets are then combined for each patient and used to diagnose or select appropriate therapy for each individual.

Universal detection assays and/or encoding reagents (e.g., pre-amplification primers) can be delivered to customers in a variety of ways. The sets of universal UniTaq primers can be preloaded on plates or fluidics devices, like Fluidigm IFCs, BioTrove OPENARRAYS™, Idaho FILMARRAY™, or Cepheid GENEXPERT™ cartridges. These sets can also be sold as kits in regular 96/384/1,536-well plates or "pre-plated" in multiple plates, so that customers only need to add tagged (e.g., by preamplification or any other linking strategy provided herein) samples to these plates.

The pre-amplification encoding primers with 5' universal segments corresponding to the universal segments of the universal detection primers can be ordered through a Web portal. The pre-amplification assays can be delivered to customers pooled, e.g., 96+192=288 primers mixed together to detect 96 SNPs. Alternatively, the pre-amplification primers can be delivered in plates, e.g., three oligos per well in a 96-well plate. The latter gives customers an additional flexibility to change the list of targets, but requires an additional step of pooling of all pre-amplification primers together. In some research applications, the same set of genes/SNPs/miRNAs is measured by different customers. In such cases, pre-amplification primers can be inventoried.

In clinical and non-research applications, pooled pre-amplification encoding primers would be particularly convenient, as all customers need to detect the same set of targets. Several pools may be bundled together, e.g., 192 SNPs detected in two colors may require two 96-SNP pre-amplification primer pools. The bundled pools may include different types of pre-amplification primers, e.g., 96 SNPs in pool one, two pools for 192 gene expression targets, one pool for 96 methylation targets, etc. These bundled pre-amplification pools can be used for clinical applications when it is desirable to measure different types of DNA (SNP, CNV, mutations, methylation, etc.) and/or RNA markers for each sample.

Example Universal Detection Composition

Figure 26:
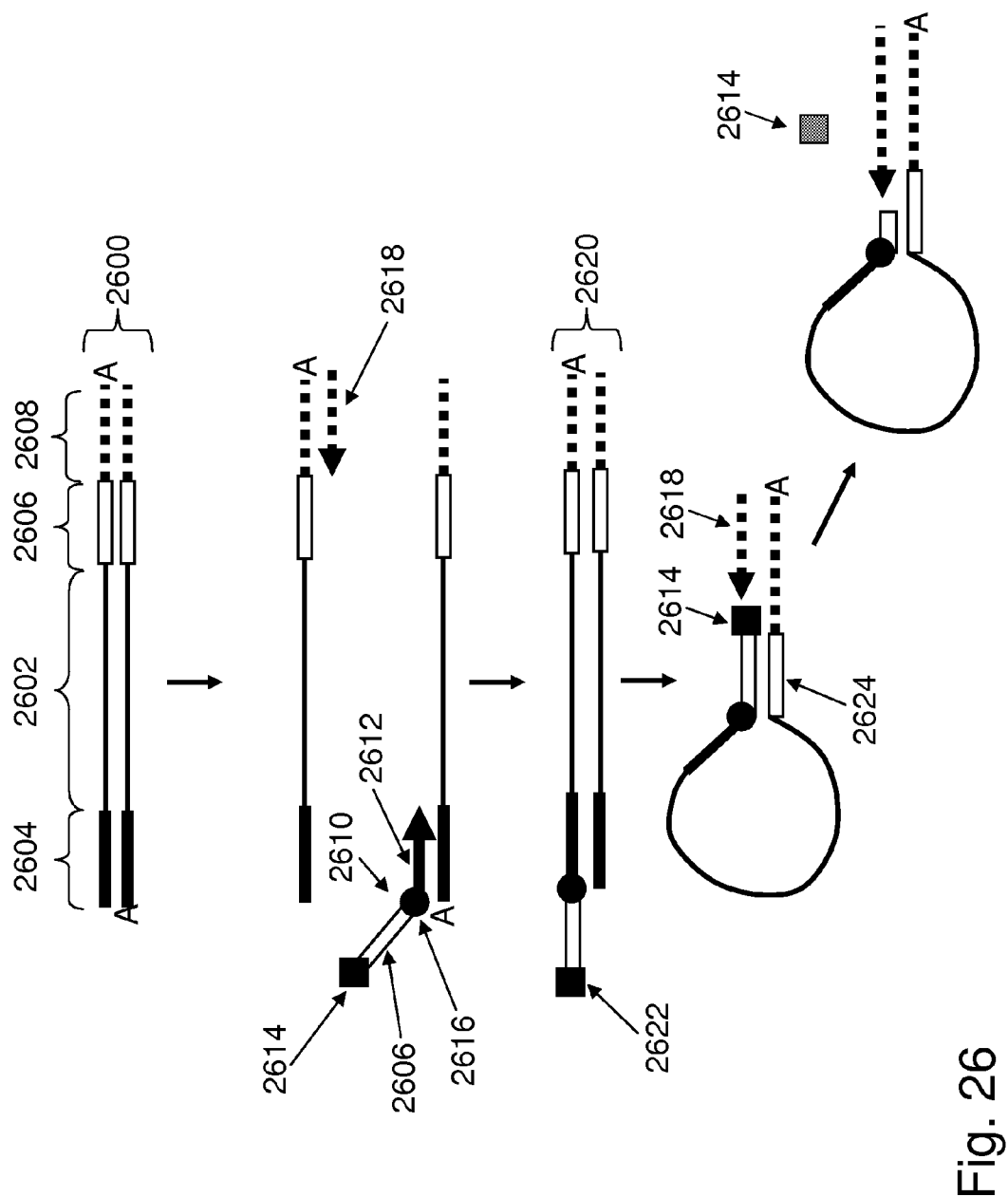
FIG. 26 schematically illustrates an example nucleic acid detection reaction mixture in accordance with the present invention.

As noted herein, the present invention provides compositions for universally detecting target nucleic acids of interest. For example, as schematically illustrated in FIG. 26, the present invention provides nucleic acid detection reaction mixtures. As shown, the reaction mixtures includes analyte nucleic acid 2600 having nucleic acid subsequence of interest 2602. The analyte nucleic acid also includes first tag sequence 2604, second tag sequence 2606 and third tag sequence 2608. As shown, the second tag sequence is located between the first and third tag sequences. The reaction mixture further includes first universal primer 2610 that includes first tag complement subsequence 2612 that is complementary to first tag sequence 2604. The first universal primer also includes a subsequence that includes second tag sequence 2606 or a subsequence thereof, and detectable label 2614. Optionally, the first universal primer includes label quencher 2616. The reaction mixture further includes second universal primer 2618 that includes the third tag sequence or a subsequence thereof. As used herein, "including the first tag sequence", "including the second tag sequence", and "including the third tag sequence" means that the first or second universal primer includes a subsequence that is sufficiently similar to the first, second, or third tag sequences such that the universal primer subsequence is capable of annealing to a complement of the first, second, or third tag sequence under the desired reaction conditions (e.g., desired temperature, etc.). Further, it will be understood that "tag sequence" includes either strand of the first, second and third tag sequences.

Methods for detecting an analyte nucleic acid using the reaction mixture as shown in FIG. 26 are also provided by the present invention. The methods include providing the reaction mixture shown in FIG. 26. One or more PCR cycles are performed. During PCR, tag complement subsequence 2612 of first universal primer 2610 anneals to first tag 2604 of the analyte nucleic acid, and second universal primer 2618 anneals to third tag sequence 2608. The one or more PCR cycles generate product 2620. Product 2620 is melted and the reaction temperature is subsequently reduced, such that second tag sequence 2606 of upper strand 2622 of product 2620 forms hairpin stem 2624 with the complementary strand of second tag sequence 2606. Following hairpin formation, second universal primer anneals to upper strand 2622 and is extended by a polymerase having 5' exonuclease activity. Extension of the second universal primer releases label 2614 from upper strand 2622, permitting detection of the label (e.g., unquenched or reduced quenched label 2614), which detection indicates the presence or amount of the target nucleic acid. As will be appreciated and described elsewhere herein, the example reaction mixtures and methods illustrated in FIG. 26 can be used (or modified for use) with any of the example universal detection formats, example universal segment linking strategies, and exemplary applications (optionally in high-throughput) provided by the present invention.

Target Nucleic Acid Sources and Molecular Biology Reagents and Techniques

As will be appreciated, target nucleic acids that find use in the invention can be obtained from a wide variety of sources. For example, target nucleic acids can be obtained from biological or laboratory samples including cells, tissues, lysates, and the like. In certain aspects, the source of target nucleic acids includes cells or tissues from an individual with a disease, e.g., cancer or any other disease of particular interest to the user.

A plethora of kits are commercially available for the purification of target nucleic acids from cells or tissues, if desired (see, e.g., EASYPREP™, FLEXIPREP™, both from Pharmacia Biotech; STRATACLEAN™ from Stratagene; QIAPREP™ from Qiagen). In addition, essentially any target nucleic acid can be custom or standard ordered from any of a variety of commercial sources.

General texts which describe molecular biological techniques for the isolation and manipulation of nucleic acids include Berger and Kimmel, Guide to Molecular Cloning Techniques, Methods in Enzymology volume 152 Academic Press, Inc., San Diego, Calif. (Berger); Sambrook et al., Molecular Cloning: A Laboratory Manual (3rd Ed.), Vol. 1-3, Cold Spring Harbor Laboratory, Cold Spring Harbor, N.Y., 2001 ("Sambrook") and Current Protocols in Molecular Biology, F. M. Ausubel et al., eds., Current Protocols, a joint venture between Greene Publishing Associates, Inc. and John Wiley & Sons, Inc., (supplemented through the current date) ("Ausubel")).

Labeling strategies for labeling nucleic acids and corresponding detection strategies can be found, e.g., in Haugland (1996) Handbook of Fluorescent Probes and Research Chemicals Sixth Edition by Molecular Probes, Inc. (Eugene Oreg.); or Haugland (2001) Handbook of Fluorescent Probes and Research Chemicals Eighth Edition by Molecular Probes, Inc. (Eugene Oreg.) (Available on CD ROM).

A number of embodiments of the present invention utilize the principles of polymerase chain reaction (PCR). PCR methods and reagents, as well as optimization of PCR reaction conditions (e.g., annealing temperatures, extension times, buffer components, metal cofactor concentrations, etc.) are well known in the art. Details regarding PCR and its uses are described, e.g., in Van Pelt-Verkuil et al. (2010) Principles and Technical Aspects of PCR Amplification Springer; 1st Edition ISBN-10: 9048175798, ISBN-13: 978-9048175796; Bustin (Ed) (2009) The PCR Revolution: Basic Technologies and Applications Cambridge University Press; 1st edition ISBN-10: 0521882311, ISBN-13: 978-0521882316; PCR Protocols: A Guide to Methods and Applications (Innis et al. eds) Academic Press Inc. San Diego, Calif. (1990) (Innis); Chen et al. (ed) PCR Cloning Protocols, Second Edition (Methods in Molecular Biology, Volume 192) Humana Press; and in Viljoen et al. (2005) Molecular Diagnostic PCR Handbook Springer, ISBN 1402034032.

As noted herein, the universal detection steps of the present invention can be performed in real-time, e.g., where one or more detectable signals (if any) corresponding to the presence or amount of one or more target nucleic acids are detected at the conclusion of one or more PCR cycles prior to completion of thermal cycling. Real-time/quantitative PCR techniques are known in the art. Detailed guidance can be found in, e.g., Clementi M. et al (1993) PCR Methods Appl, 2:191-196; Freeman W. M. et al (1999) Biotechniques, 26:112-122, 124-125; Lutfalla G. and Uze G. (2006) Methods Enzymol, 410: 386-400; Diviacco S. et al (1992) Gene, 122: 313-320 Gu Z. et al (2003)/.Clin. Microbiol, 41: 4636-4641. Real-time (e.g., quantitative) PCR detection chemistries are also known and have been reviewed in, e.g. Mackay J., Landt O. (2007) Methods Mol. Biol, 353: 237-262; Didenko V. V. (2001) BioTechniques, 31, 1106-1121; and Mackay L M. et al (2002) Nucleic Acids Res., 30: 1292-1305, which are incorporated herein by reference in their entireties for all purposes.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

What is claimed is:

1. An analyte nucleic acid detection reaction mixture, used to detect a target nucleic acid subsequence of interest, the mixture comprising:
   an analyte nucleic acid comprising the target nucleic acid subsequence of interest, the analyte nucleic acid further comprising first, second and third tag sequences, the second tag sequence being located between the first and third tag sequences; and both the first and the second tag sequences are universal tag sequences;
   a first universal primer comprising a first tag complement subsequence that is complementary to the first tag sequence, a subsequence that comprises the second tag sequence, and a detectable label; and,
   a second universal primer comprising a sequence that comprises the third tag sequence.

2. The reaction mixture of claim 1, wherein the mixture further comprises a complementary nucleic acid comprising subsequences complementary to the nucleic acid subsequence of interest and the first, second and third tag sequences.

3. The reaction mixture of claim 1, wherein the nucleic acid subsequence of interest comprises a nucleic acid or nucleic acid feature selected from: a DNA, an RNA, a primate nucleic acid, a rodent nucleic acid, a viral nucleic acid, a bacterial nucleic acid, an archaea nucleic acid, a cDNA, a cDNA corresponding to a short RNA, a genetic variant, a mutation or insertion that confers drug resistance, a somatic mutation, a polymorphism, a single nucleotide polymorphism, a rare allele, a portion of the KRAS gene, a nucleic acid that exhibits a variation in copy number, an intron, an exon, an intron-exon boundary, a splice junction, one or more dinucleotides corresponding to one or more methylated or unmethylated CpG dinucleotides, a nucleic acid comprising one or more restriction enzyme recognition sequences, a portion of human chromosome 21, a portion of the human X chromosome, and a portion of the human Y chromosome.

4. The reaction mixture of claim 1, wherein the first universal primer comprises a label quencher disposed at an effective quenching distance from the label.

5. The reaction mixture of claim 4, wherein the label quencher is located between the first tag complement subsequence and the subsequence that comprises the second tag sequence, and wherein the label is located on an end opposite the subsequence that comprises the second tag sequence, as compared to the label quencher.

6. The reaction mixture of claim 4, wherein the label is located between the first tag complement sequence and the subsequence that comprises the second tag sequence, and wherein the label quencher is located on an end opposite the subsequence that comprises the second tag sequence, as compared to the label.

7. The reaction mixture of claim 4, wherein the first universal primer comprises a polymerase blocking unit between the first tag complement and second tag sequence.

8. The reaction mixture of claim 1, wherein the label is a fluorescent label.

9. The reaction mixture of claim 1, wherein first universal primer is configured to generate a detectable signal when the 3' end of the first universal primer is extended.

10. The reaction mixture of claim 1, further comprising:
    a second analyte nucleic acid comprising a second target nucleic acid subsequence of interest, the second analyte nucleic acid further comprising fourth, fifth and sixth tag sequences, the fifth tag sequence being located between the fourth and sixth tag sequences;
    a third universal primer comprising a second tag complement subsequence that is complementary to the fourth tag sequence, a subsequence that comprises the fifth tag sequence, a label and a label quencher, wherein the label of the second universal label primer is different from the label of the first universal label primer; and,
    a fourth universal primer comprising a sequence that comprises the sixth tag sequence.

11. The reaction mixture of claim 10, wherein the sixth tag sequence and the third tag sequence are the same.

12. The reaction mixture of claim 10, wherein the second nucleic acid subsequence of interest comprises a nucleic acid or nucleic acid feature selected from: a DNA, an RNA, a bisulphite treated DNA, a primate nucleic acid, a rodent nucleic acid, a viral nucleic acid, a bacterial nucleic acid, an archaea nucleic acid, a cDNA, a cDNA corresponding to a short RNA, a genetic variant, a mutation or insertion that confers drug resistance, a somatic mutation, a polymorphism, a single nucleotide polymorphism, a rare allele, a portion of the KRAS gene, a nucleic acid that exhibits a variation in copy number, an intron, an exon, an intron-exon boundary, a splice junction, one or more dinucleotides corresponding to one or more methylated or unmethylated CpG dinucleotides, a nucleic acid comprising one or more restriction enzyme recognition sequences, a portion of human chromosome 21, a portion of the human X chromosome, and a portion of the human Y chromosome.

13. The reaction mixture of claim 10, wherein the first nucleic acid subsequence of interest comprises a cDNA sequence corresponding to an mRNA expressed from a first gene, and wherein the second nucleic acid subsequence of interest comprises a cDNA sequence corresponding to an mRNA expressed from a second gene.

14. The reaction mixture of claim 1, wherein the first universal primer comprises two oligonucleotides attached to a surface at a density such that 3' and 5' solution ends of the two oligonucleotides are spatially close to each other so as to function as two ends of the first universal primer.

15. The reaction mixture of claim 1, wherein the first universal primer comprises the second tag sequence and a complement of the first tag sequence and, and the second universal primer comprises the third tag sequence.

16. The reaction mixture of claim 1, wherein the nucleic acid sequence of interest does not comprise the second tag sequence.

17. The reaction mixture of claim 1, further comprising:
a second analyte nucleic acid comprising a second nucleic acid sequence of interest, the second analyte nucleic acid further comprising fourth, fifth, and sixth tag sequences, the fifth tag sequence being located between the fourth and sixth tag sequences;
a third universal primer comprising a fourth tag complement sequence, the fifth tag sequence, a label and a label quencher, wherein the label of the second universal primer is the same as the label of the first universal primer; and,
a fourth universal primer comprising a sequence that comprises the sixth tag sequence.

18. The reaction mixture of claim 17, wherein the fourth tag sequence is the same as the first tag sequence of the first analyte nucleic acid.

19. The reaction mixture of claim 1, wherein the analyte nucleic acid is a construct wherein the target nucleic acid subsequence of interest is a natural genomic sequence, and the second tag sequence is not a sequence naturally found adjacent to the subsequence of interest.

20. The reaction mixture of claim 19, wherein the second or third tag sequence was previously attached to the sequence of interest in a PCR extension reaction.

21. The reaction mixture of claim 19, wherein the first or second tag sequence was not previously attached to the sequence of interest before a polymerase extension of the target sequence of interest.

22. The reaction mixture of claim 1, wherein the mixture has not been exposed to a polymerase extension reaction or does not comprise a DNA polymerase.

23. The reaction mixture of claim 1, wherein the analyte nucleic acid has not been transcribed by extension from the first universal primer.

24. The reaction mixture of claim 1, wherein the analyte nucleic acid comprises sequences in the order of: first tag sequence, target nucleic acid of interest sequence, second tag sequence.

25. The reaction mixture of claim 1, wherein the mixture is configured so that extension of the first universal primer along the analyte nucleic acid provides an extension product comprising sequences in the order of: complement of the first tag sequence, complement of the nucleic acid of interest sequence, and complement of the second tag sequence.

26. The reaction mixture of claim 25, wherein extension of the first universal primer along the analyte nucleic acid provides an extension product comprising the features in the order of: the detectable label, the second tag sequence, complement of the first tag sequence, complement of the nucleic acid of interest sequence, complement of the second tag sequence.

27. The reaction mixture of claim 1, wherein extension of the first universal primer along the analyte nucleic acid provides an extension product comprising the features in the 3' to 5' order of: the second tag sequence, complement of the first tag sequence, complement of the nucleic acid of interest sequence, complement of the second tag sequence.

28. The reaction mixture of claim 1, wherein the first tag sequence is a universal tag sequence complementary to the first universal primer and third tag sequences is a universal tag sequences complementary to the second universal primer.

29. The reaction mixture of claim 1, wherein the universal tag sequences are not related to the nucleic acid of interest.

* * * * *